(12) United States Patent
Eschen et al.

(10) Patent No.: US 11,993,874 B2
(45) Date of Patent: May 28, 2024

(54) TOPOGRAPHICALLY CONFORMING GARMENTS

(71) Applicant: Regents of the University of Minnesota, Minneapolis, MN (US)

(72) Inventors: Kevin Eschen, Minneapolis, MN (US); Julianna Abel, Minneapolis, MN (US); Bradley Thomas Holschuh, North Oaks, MN (US); Rachael Margaret Granberry, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/753,722

(22) PCT Filed: Sep. 11, 2020

(86) PCT No.: PCT/US2020/050495
§ 371 (c)(1),
(2) Date: Mar. 11, 2022

(87) PCT Pub. No.: WO2021/050944
PCT Pub. Date: Mar. 18, 2021

(65) Prior Publication Data
US 2022/0338577 A1   Oct. 27, 2022

Related U.S. Application Data

(60) Provisional application No. 62/900,154, filed on Sep. 13, 2019.

(51) Int. Cl.
*D04B 1/26* (2006.01)
*A41D 31/18* (2019.01)
(Continued)

(52) U.S. Cl.
CPC ............ *D04B 1/265* (2013.01); *A41D 31/18* (2019.02); *A43B 1/04* (2013.01); *A43B 23/0265* (2013.01);
(Continued)

(58) Field of Classification Search
CPC ... D04B 1/10; D04B 1/18; D04B 1/24; D04B 1/265; D04B 21/06; D04B 21/207; A61F 13/08; D10B 2509/028; D10B 2501/043
See application file for complete search history.

(56) References Cited

U.S. PATENT DOCUMENTS 7,043,329 B2 * 5/2006 Dias ..................... D04B 15/50
66/55
7,895,863 B2 * 3/2011 Smith ..................... A61F 13/08
66/172 E
(Continued)

FOREIGN PATENT DOCUMENTS

WO    WO 2011/135243 A1    11/2011
WO    WO-2021050944 A1 *    3/2021    ............. A41D 31/18

OTHER PUBLICATIONS

International Search Report, International Application No. PCT/US2020/050495, dated Feb. 4, 2021, 3 pages.

*Primary Examiner* — Danny Worrell
(74) *Attorney, Agent, or Firm* — Merchant & Gould P.C.

(57) ABSTRACT

Advances in actuating fabrics could enable a paradigm shift in the field of smart wearables by dynamically fitting themselves to the unique topography of the human body. Active fabrics and fitting mechanisms are described herein that enable garments to conform around surface concavities without requiring high elasticity or a multiplicity of closure devices. Advanced materials and systems innovations (1) enable novel garment manufacturing and application strategies, (2) facilitate topographical fitting (spatial actuation) through garment architectural design, and (3) provide tun-
(Continued)

able NiTi-based SMA actuation temperatures to enable actuation on the surface of human skin. Such fabrics and garments are usable in a variety of fields including medical compression, technical sportswear, exosuits, space suits and components thereof, or non-garment applications.

19 Claims, 23 Drawing Sheets

(51) Int. Cl.
| | |
|---|---|
| *A43B 1/04* | (2022.01) |
| *A43B 23/02* | (2006.01) |
| *A61F 13/08* | (2006.01) |
| *D04B 1/10* | (2006.01) |
| *D04B 1/18* | (2006.01) |
| *D04B 1/24* | (2006.01) |
| *D04B 21/06* | (2006.01) |
| *D04B 21/20* | (2006.01) |

(52) U.S. Cl.
CPC ............... *A61F 13/08* (2013.01); *D04B 1/10* (2013.01); *D04B 1/18* (2013.01); *D04B 1/24* (2013.01); *D04B 21/06* (2013.01); *D04B 21/207* (2013.01); *A41D 2500/10* (2013.01); *D10B 2401/046* (2013.01); *D10B 2501/04* (2013.01); *D10B 2501/043* (2013.01); *D10B 2509/028* (2013.01)

(56) References Cited

U.S. PATENT DOCUMENTS

| | | | | |
|---|---|---|---|---|
| 8,317,736 | B2 * | 11/2012 | Virkus | A61F 13/08 |
| | | | | 602/61 |
| 10,842,680 | B1 * | 11/2020 | Weiler | G16H 20/00 |
| 10,982,359 | B2 * | 4/2021 | Roe | D04B 1/108 |
| 11,560,651 | B2 * | 1/2023 | Rock | D04B 1/102 |
| 2016/0340814 | A1 | 11/2016 | Ridley et al. | |
| 2019/0017199 | A1 * | 1/2019 | Granberry | B32B 5/026 |
| 2019/0343216 | A1 | 11/2019 | Huffa et al. | |

* cited by examiner

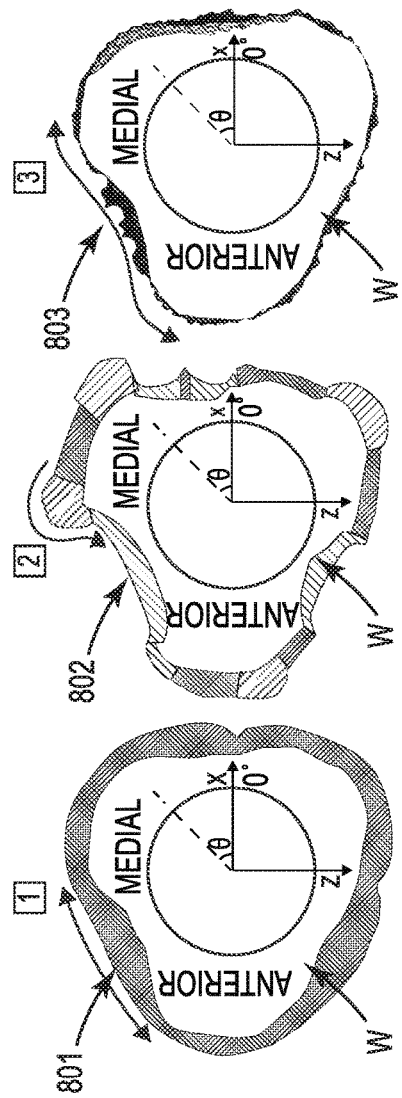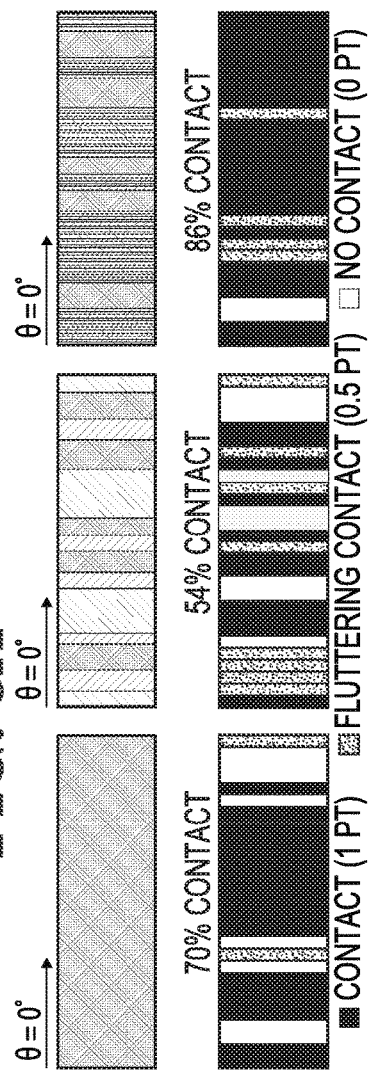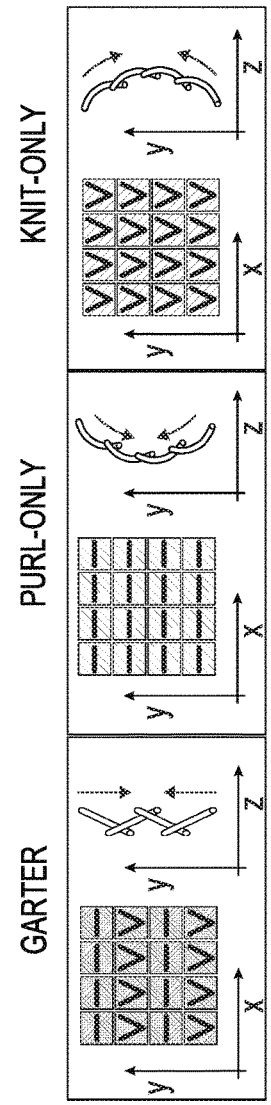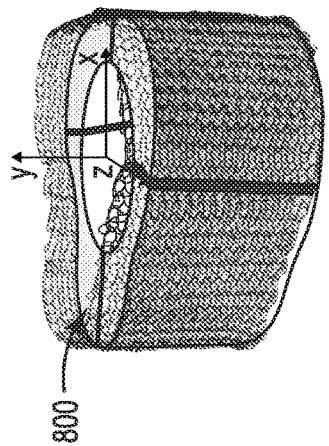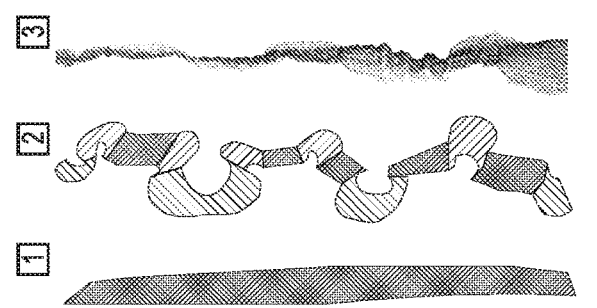
FIG. 8A
FIG. 8B
FIG. 8C

TOPOGRAPHICALLY CONFORMING GARMENTS

PRIORITY CLAIM

The present application is a National Phase entry of PCT Application No. PCT/US2020/050495, filed Sep. 11, 2020, which claims the benefit of U.S. Provisional Application No. 62/900,154 filed Sep. 13, 2019, the contents of which are hereby incorporated herein in their entirety by reference.

TECHNICAL FIELD

Embodiments relate to materials that can produce functional effects in desired locations, patterns, and quantities for use in a variety of applications. Additionally, embodiments relate to fabrics and garments produced from such materials, and methods of making such materials, fabrics, and garments. Some embodiments described herein relate to use of shape memory knit patterns or panels that transition to a tensioned state to produce a tailored fit over concave and convex topographies while maintaining a desired level (or set of levels) of compression across the entire garment. Some embodiments described herein relate to devices for adjusting or maintaining mechanical tension, including use of tension limiting switches in shape memory fabrics, or the use of shape memory panels that transition to a tensioned, superelastic state upon donning or removal from a cooled environment, to provide garments that are easy to don and doff or produce a tailored fit for most wearers without the use of conventional fasteners.

BACKGROUND

Maintaining desired compression levels in fabrics or garments is a technical challenge in a variety of industries. For example, medical compression requires providing a therapeutic quantity of force across each particular area to accomplish a desired medical outcome. The level of force may be constant or it could be variable, both with respect to position and with respect to time. In other industries, such as garments incorporating diagnostic sensors or haptic feedback systems, maintaining physical contact sufficient to acquire or deliver a signal is desirable. Fabrics or woven materials that provide desired shape changes or compression changes can have benefits outside of worn garments, as well.

With respect to medical compression garments, worn articles of clothing can apply pressure to the body either through garment reduction (e.g., knit elastane shapewear) or through inflation (e.g., a blood pressure cuff). Compression is an effective medical treatment for disorders ranging from varicose veins and lymphedema to orthostatic intolerance and deep vein thrombosis.

Conventional compression garments, including elastic compression sleeves and inflatable compression systems, may aid in relief of these conditions but are also limited in usability. Fixed levels of compression in elastic materials may induce challenges in donning/doffing, complicating patient compliance. Conventional compression garments rely upon either under-sized or inflatable compression technologies. Under-sized elastic garments are typically associated with a particular portion of a user's body, such as a calf or forearm. The cross-section of the garment when relaxed is smaller than the cross-section of the portion of the body. When applied, the garment stretches and exerts force as the elastic contracts back towards its relaxed size. Other types of non-elastic, undersized compression technologies include oversized garments that can be made undersized by reducing the garment circumference after the garment has been donned by adjustable mechanisms, such as lacing, buckles, hook and loop tape, or straps.

Under-sized garments apply a substantially constant pressure on the portion of the user's body at each particular point, but only based on the assumption that the anatomy is substantially circular in cross-section. Depending on the user's actual anatomy, however, the amount of pressure can vary along the length of the garment or around the garment. Although under-sized garments can be designed to provide substantially uniform pressure (or a desired pressure gradient) in the ideal case, variations in user anatomy can result in variation from the intended pressure profile for that garment. Compression garments that rely on elasticity of the material itself can exhibit "bridging," whereby compression is high on convex portions of the wearer's anatomy while the material only lightly compresses, or even fails to make contact with, concave portions of the anatomy. This uneven pressure can adversely affect the effectiveness of some types of garments, especially for some medical applications, but also any form-fitting wearable that relies on body proximity for functionality. Examples include, but are not limited to those that provide haptic feedback to the wearer, or those that rely upon electrical contact with the wearer.

In addition to medical context, garments with compression features have been used for aesthetic reasons. Aesthetics can be a key factor in adoption of a garment by consumers or by a patient who would benefit from wearing a compression garment, as unattractive design leads to dissatisfaction and noncompliance. Even where no therapeutic level of compression is needed, "athleisure" clothing has become popular, including which garments that exhibit some compressive force and are made to be stylish, form fitting, or shaping, as well as comfortable. Examples include leggings or active footwear, for example. Some conventional athleisure garments use elastomeric components and stretch to create a desired shape profile, and bridging can again be detrimental. Additionally, consumer shapewear applies high-levels of compression around target body locations to produce an aesthetic silhouette and requires conformity around complex body shapes.

Athletic garments can include variable compression for particular non-aesthetic benefits, also. These garments, commonly referred to as "technical sportswear," provide some performance-enhancing benefit such as streamlining, preventing injury by regulating movement patterns, or increasing circulation to specific muscles. In some technical sportswear, increases in temperature can be used to actuate a change in the properties of the garment, such as to provide targeted support for an overexerted muscle.

The pressure profile created by a garment (whether used for a medical or aesthetic purpose) can vary based upon the way in which it is used. The cross-sections of various body parts change dynamically depending upon whether the person is seated, standing, or lying down. Therefore, an under-sized garment, which typically cannot be resized or reshaped depending on the user's activity level or body position, may apply different levels of compression for users with different levels or types of activity.

Undersized compression garments do not provide tailored compression and can be too tight or too loose (or both, depending on the area), and bridging prevents electrical contact, formation of desired shape, or even a lack of sufficient 'anchoring' to the user. Anchoring can be created by providing compression about the wearer's body at some location against which tension can be applied. If the compression is strong enough and the profile of the garment matches the wearer's body, a mechanical interference fit is created and force can be applied, such as in a garment used in physical therapy. If the garment bridges, then the interference fit can be lost.

Wearable robotic devices are plagued with fit and sizing obstacles due to the challenges of achieving accurate system fit across populations with vast anthropometric variability. Unintended system fit around the body results in user discomfort and diminished system power (up to 50% noted) from system drift and unintended compliance. Wearable robotic systems have traditionally utilized physical interfaces such as braces, cuffs, and even textiles to anchor robotic systems to the human body. While the textile-interface approach increases user comfort compared to rigid braces and cuffs, passive fabrics are unable to conform around surface concavities and require a multiplicity of closure devices (sometimes biaxial) to achieve accurate garment fit across a user population. All physical interface solutions require wearable robotic systems to be fully- or partially-customized to fit the user or sized (e.g. small, medium, large, etc.) through traditional wearable product sizing methods. Standardized sizes are problematic for wearable robotics because size runs reduce the fit accuracy of a wearable system, resulting in wearability and system function issues (e.g. drift, placement) that ultimately inhibits usability and marketability.

Postural orthostatic tachycardia syndrome (POTS) is a clinical autonomic disorder characterized by a spike in heart rate and syncope in response to orthostasis, symptoms which then dissipate upon recumbence. Additional symptoms include chronic fatigue, bloating, and nausea. POTS predominately effects females (5:1) between the ages of 15 and 50 years. It is estimated 1 to 3 million are affected by POTS in the United States. While there is no known cure, symptom management requires a multifaceted approach, including physical exercise, counter maneuvers, high salt and fluid intake, and medications, including beta blockers and fludrocortisone. Lower body compression is a core component to POTS treatment, especially during prolonged periods of upright posture. Because POTS disproportionately affects young, otherwise healthy females who often have high physical and professional demands, compression garments can be critical to allowing this population to carry out their activities of daily living.

Pneumatic and undersized compression garments are currently available to the consumer population for treatment of POTS. Compression can also be an effective medical treatment for disorders ranging from varicose veins and lymphedema to orthostatic intolerance and deep vein thrombosis. Inflatable garments provide effective, medically therapeutic pressures to the body. These inflatable garments such as leg sleeves are bulky, tethered to an inflation source, and inhibit joint mobility. Undersized compression garments are a more practical solution for POTS patients, who are predominately symptomatic during periods of activity. Elastic knit stockings are low-profile and do not inhibit mobility, but they can exert unpredictable pressures and physicians report a high level of non-compliance amongst patients due to donning difficulties and reported discomfort.

Other types of functional fabrics can provide other types of benefits. For example, functional fabrics can provide visual or auditory output, or they can be used for energy storage and conversion, or to monitor health or activity of a wearer. Functional fabrics also included components of heated garments that convert some type of energy, such as electrical energy stored in a battery, into thermal energy. Conventionally, wires, leads, or sensors can be inserted into fabrics, or fabrics can be formed around such objects, to provide the ancillary benefit of the functional fabric.

Shape memory alloys, and other smart materials, such as shape memory polymers and carbon nanotubes, can be electrically-controlled as a means to induce thermo-mechanical transformation which transforms a less-stiff material to an activated, higher-stiffness material through heating. These states are referred to as martensite and austenite, respectively. Shape memory polymers could undergo a glassy or crystalline phase transformation and carbon nanotubes can use thermal expansion to change stiffness. A solution is needed to the problem of providing good interference fit for all of the uses described above, and others.

SUMMARY

According to a first embodiment, a fabric is configured to conform to a 3D topography. The fabric comprises a first knitted portion having a first knit pattern corresponding to a concave portion of the 3D topography, and a second knitted portion having a second knit pattern corresponding to a convex portion of the 3D topography. The first knitted portion and the second knitted portion can each include a shape memory component. The knit pattern of the first knitted portion is different from the knit pattern of the second knitted portion such that upon actuation of the shape memory component the first portion contracts and forms a concave shape while the second portion contracts and forms a convex shape.

Optionally, the fabric can further include a third knitted portion having a third knit pattern corresponding to a flat portion of the 3D topography, wherein the third knit pattern includes a shape memory component and has a knit pattern that is different from the knit pattern of both the first knitted portion and the second knitted portion. The third knitted portion can be configured to contract and remain substantially flat when the shape memory material exceeds a transition temperature. The contraction of the shape memory can cause the fabric to conform to the 3D topography with a uniform level of compression across both the concave portion and the convex portion. The fabric can further include a passive portion comprising a material that is not a shape memory material. The shape memory material can include multiple shape memory alloys, each of the multiple shape memory alloys having a corresponding transition temperature. The fabric can form a garment, and the 3D topography could be, for example, a foot, a hand, or a leg.

According to another embodiment, a method for forming a topographically conforming garment comprises collecting anthropometric data from a wearer to form a 3D topography, the anthropometric data comprising a series of closed loops arranged around a central axis. The method further comprises determining the second derivative of the radius of each one of the series of closed loops with respect to angle around the central axis to categorize sections of each of the series of closed loops into convex portions, concave portions, and flat portions. The method further comprises generating an initial design in which concave portions are knitted with Jersey purl stitch, flat sections are knitted with garter stitch, and convex portions are knitted with Jersey knit stitch, wherein the initial design includes a shape memory material incorporated into each of the sections such that exceeding a transition temperature of the shape memory material causes the Jersey purl stitch to contract and form a concave shape, the garter stitch to contract while remaining flat, and the Jersey knit stitch to contract and form a convex shape. The method can incorporate a closing mechanism, such as zippers, laces, or snaps, such that topographical conforming occurs directly upon activation. The method can also exclude a closing mechanism. In the latter case, the garment is initially oversized and must contract upon activation to achieve the reduced dimensions of the body before topographical conformation can occur. The latter method comprises calculating donning and doffing ease corresponding to the initial design, and iteratively modifying the design to achieve a desired minimum level of actuation contraction and a maximum size difference between the garment and the anthropometric data while maintaining a desired level of donning and doffing ease.

Iteratively modifying the design can optionally further comprise maintaining a filament diameter difference beneath a threshold. In embodiments, a plurality of panels are combined via stitching to form the iteratively modified design or the fabric, each of the panels comprising at least one of a convex portion, a concave portion, or a flat portion.

Embodiments can further include providing a topographically conforming garment as described above. Such embodiments can include arranging the topographically conforming garment on the wearer and heating the garment to a transition temperature of the shape memory material of the concave portions, the convex portions, and the flat portions to achieve a desired compression profile on the wearer. The compression profile can be uniform in some embodiments. The method can include providing a topographically conforming garment for any of a foot, a hand, or a leg, for example.

Iterating the design as described above can be performed manually or via a machine learning algorithm, in embodiments.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 8A-8C depict iterative improvements in garments for a complex topography according to an embodiment.

Figure 1A:
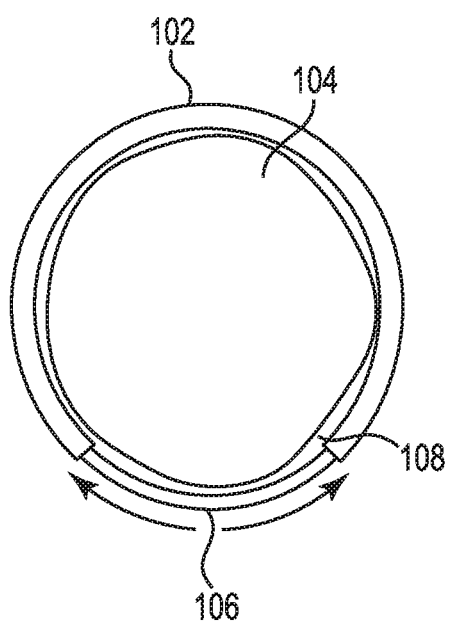
FIGS. 1A and 1B depict cross-sectional views of an unactivated and activated garment, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Functional fabrics of all types described herein can provide actuation, sensing, energy harvesting, and communication as intrinsic fabric properties by integrating multifunctional fibers into designed textile geometries. The fiber material and the textile architecture can be designed to achieve functional fabric characteristics such as distributed actuation and sensing, variable stiffness, and complex, three-dimensional deformations. Through geometric design on the macroscopic and mesoscopic scales, knitted functional fabrics can achieve complex actuation deformations, such as corrugation, scrolling, and contraction. Additional, microscopic design parameters can be selected by the choice of multifunctional fiber and its specific material properties. Specific patterns and materials can be used to generate desired compression for either therapeutic, aesthetic, or other functional purposes such as the elimination of traditional fasteners that are required for non-compressive fabrics.

According to embodiments described herein, an active fabric includes a first plurality of filaments, each of the first plurality of filaments comprising an active material. Such active filaments may, in embodiments, be interspersed with passive materials, which are defined herein as those materials that do not undergo a superelastic transition upon exceeding a transition temperature. As such, active fabrics will experience a shape or size change at a predetermined temperature to generate a change in the overall fabric.

Throughout this disclosure, several specialized terms related to active knitted fabrics are used. The first is "knit index," which is the ratio of the area of a loop of active material enclosed in the martensite state and the square of the active knit material wire diameter. Depending on the knit index among other factors, a functional fabric with desired properties can be created. Two particularly important properties are the pressure applied by the fabric (i.e., how forcefully a garment made of the active fabric squeezes when the active material is actuated) and the actuation contraction of the fabric (i.e., the normalized difference of the unactuated and actuated fabric lengths). Actuation contraction of an active knit fabric is a function of the martensite length $l_M$ and the austenite length $l_A$:

$$\zeta=(l_M-l_A)/l_M.$$

Depending on the knit index, the diameter of the active material, and other factors, different types of active fabrics can be created. One type of fabric is referred to herein as a "therapeutic compression garment," and it is designed primarily to provide a therapeutic level of compression to a wearer. Accordingly, the level of force applied by the fabric when activated should preferably reach a desired minimum level, while the total actuation contraction is of lesser importance.

A second type is referred to as a "self-fitting" garment, which is not intended to provide therapeutic compression but rather to contract to an accurate fit for the wearer. Accordingly, the level of force applied by the garment should be smaller than that of a therapeutic compression garment, while the total displacement should be larger. Other garments, fabrics, or portions thereof can be made of "passive" material, which refers to materials that do not exhibit a shape-memory transition.

In some embodiments, the shape memory alloy elements are configured to change between martensite and austenite forms upon donning the garment, based on ambient conditions. For example, in some embodiments exposure to room temperature causes the garment to change from martensite to austenite. Alternatively, in other embodiments exposure to skin temperature is sufficient to cause the garment to change from martensite to austenite. The shape memory transition causes compression of the garment, such that an initially loose-fitting garment will become a compression garment that is tight fitting up to, and including, tight enough to act as a clinical compression garment.

Materials are described herein that can be used to generate active fabrics, including fabrics that include active components in specific locations. Filaments are described herein that include multiple heterogeneous portions, at least some of which are made of active materials. Active materials are those that have some active or functional properties, such as actuatable mechanical components (e.g., piezoelectrics, electro-mechanical components, thermo-mechanical components, and shape memory materials), electrically functional components (e.g., conductive, semiconductive, or photoelectric materials), or actuatable thermal components (e.g., materials that undergo exothermic or endothermic reactions upon exposure to stimulus, or electrically resistive materials that produce heat upon exposure to an electrical potential).

"Shape memory" or "superelastic" materials are described herein. These terms refer generally to materials that respond to changes in temperature or applied stress or strain in a pseudoelastic manner based on a phase transformation between austenitic and martensitic phases. Shape memory alloys are the most common example of shape memory materials, but this disclosure is not limited to such materials. In general, when referring to shape memory or superelastic materials, any material that undergoes such phase transitions can be used unless otherwise specified. Recently, pseudoelastic effects have been observed in protein backbones or polyurethane ionomers, for example, which are not conventional shape memory alloys but which could be used to form fabrics exhibiting shape memory effects.

According to embodiments described herein, a fabric includes an arrangement of segments, each segment having a different knit pattern, knit index, or both. By arranging the segments in a pattern or complex shape such as a garment, a resulting 3-dimensional contour can be created that includes concave, convex, or flat sections as desired, as well as more complex three-dimensional shapes. For example, a fabric could be concave in one dimension while being convex in another, commonly referred to as a "saddle point," or any other combination of flat, concave, or convex in each direction. In the context of a garment, for example, a wearer's anatomy or a desired compression profile can be created to ensure a pressure profile that accomplishes objectives such as medical compression, fit for aesthetic purposes (e.g., for athleisure garments), maintaining contact for diagnostics, or providing functional fit (e.g., for technical sportswear or for use in low-pressure environments such as space suits). It should be understood that while the embodiments described below relate to garments and clothing, other uses are equally useful in any circumstance where creating a profiled or three-dimensional fabric are also contemplated.

Topographically conforming actuators use unique properties of multifunctional materials that result in changes of stiffness and strain as a function of thermal, electrical, optical, chemical, or magnetic inputs within traditional knitted textiles to provide large 3D actuation deformations. "Self-fitting" fabrics and garments, which contract radially from an oversized shape to a fitted one, are described herein not only for circular garments but for those with complex shapes that include both convex and concave regions. Due to the topographical complexity of the human body, this complexity results in more accurate fitting as concave topographies are no longer "spanned" or "bridged," and convex topographies are compressed by the self-fitting garment. The topographically self-fitting garments described herein use different knit patterns to form grid patterns and produce functionally-graded 3D deformations in addition to the circumferential contraction of the self-fitting garment. Complex concave and convex topographies can be fitted through the design of grid patterns that connect various knit patterns (with their specific 3D actuation deformations) in a single garment. This fitting approach is a paradigm shift to smart wearables as topographical fitting and uniform compression is made available in a garment.

Advances in actuating fabrics could enable a paradigm shift in the field of fabrics such as smart wearables by dynamically fitting themselves to the unique topography of the human body. Applications including soft wearable robotics, continuous health monitoring, and body-mounted haptic feedback systems are dependent upon simultaneous body proximity and garment stiffness for functionality. Passive fabrics and fitting mechanisms are unable to conform around surface concavities and require either high elasticity or a multiplicity of closure devices to achieve garment fit. The design, manufacture, and validation of the first circumferentially-contractile and topographic self-fitting garments composed of NiTi-based Shape Memory Alloy (SMA) knitted actuators that dynamically conform to the unique shape and size of the wearer's body in response to a change of the garment's temperature is introduced. Advanced materials and systems innovations enable novel garment manufacturing and application strategies, facilitate topographical fitting (spatial actuation) through garment architectural design, and provide tunable NiTi-based SMA actuation temperatures to enable actuation on the surface of human skin. The embodiments disclosed herein are representative of a paradigm shift for wearable applications by redefining garment fit to fully-topographical conformation to the wearer through advanced materials and structures design.

Fit is not equivalent with tightness, but rather is defined by the proximity between the body and the wearable. Bodies are non-cylindrical and have non-cylindrical cross-sections; therefore, wearables (i.e., garments or body-worn articles) are often required to conform around complex body topography. Conformation is particularly important for functional wearables, such as medical compression wraps, haptic garments, or joint braces. Passive fabrics are unable to conform around concave surfaces. Active fabrics (e.g., SMA knitted actuators) offer the unique opportunity to conform fully around concave and convex body surfaces to achieve accurate fit.

Topographically-fitting SMA knitted actuators would be commercially applicable in a large range of industries, including general consumer (e.g., bras, self-fitting clothing, shoe tops, waist bands, wrist watches, hats, etc.), wearable tech (e.g., incorporated into shirt to anchor ECG monitor, smart watch, haptic feedback garments, etc.), sports clothing (e.g., targeted compression clothing, shin guards, hats, shoes, etc.), medical garments (e.g., compression garments, wearable health monitoring, prosthetic socket fitting, bracing, etc.), aerospace (e.g., orthostatic intolerance garments, mechanical counterpressure suits, vertical loading garments, etc.), and even military (e.g., impact protection, tourniquets, etc.). Because human bodies are generally non-cylindrical, modifications of the SMA knitted actuator architecture to achieve spatial actuation that matches the contours of the body (i.e., topography) would be beneficial in all wearable applications using SMA knitted actuators.

Figure 1B:
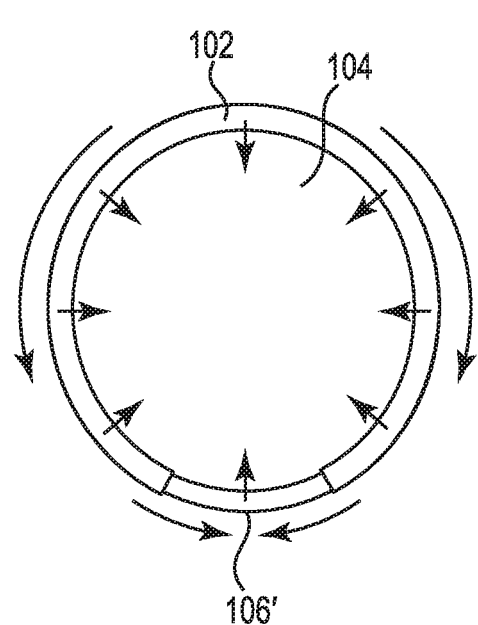

FIGS. 1A and 1B depict a garment 102 surrounding a wearer 104. In the embodiment shown in FIGS. 1A and 1B, the active compression of active component 106 in a loose, martensitestate to the active component 106' having a tensed, austenitestate causes inward compression of the overall garment 104, as depicted by the arrows in FIG. 1B. Various factors can affect the level of compression, both in terms of overall displacement (indicated by the arcuate arrows in FIG. 1B) as well as in terms of maximum compressive force that the garment can apply (indicated by the straight arrows in FIG. 1B). These features of the garment are based upon the type and amount of functional fabric used.

FIGS. 1A and 1B are simplified in that the cross-section of the wearer 104 is almost perfectly circular. In practice, the cross-section of a garment used in almost any of the fields described previously, such as technical sportswear, medical compression, athleisure, or inflatable protective garments for use in space, are far more complex and are intended to cover cross-sections that are non-cylindrical. In some contexts, the garment should provide higher levels of compression to create shaping effects, such as for technical sportswear or athleisure. In others, reduced pressure at key points can be beneficial, such as reducing the pressure on the metacarpal joint of an astronaut to prevent delamination of the fingernail as described above. In still others, the body contours of a garment will create bridging effects when uniform compression is used, inhibiting diagnostics via built-in sensors. For example, a heart-rate monitor that operates by detecting pulses or electrical signals at the user's skin will be ineffective if the sensor is arranged on a portion of the fabric of a garment that bridges away from the wearer during stretching or exercise. Similarly, bridging can prevent haptic signals from being delivered to the wearer. The top of a wearer's wrist, for example, may be convex in shape such that a smartwatch providing a haptic response will go undetected if that watch bridges across the top of the wrist rather than making direct contact.

Figure 2:
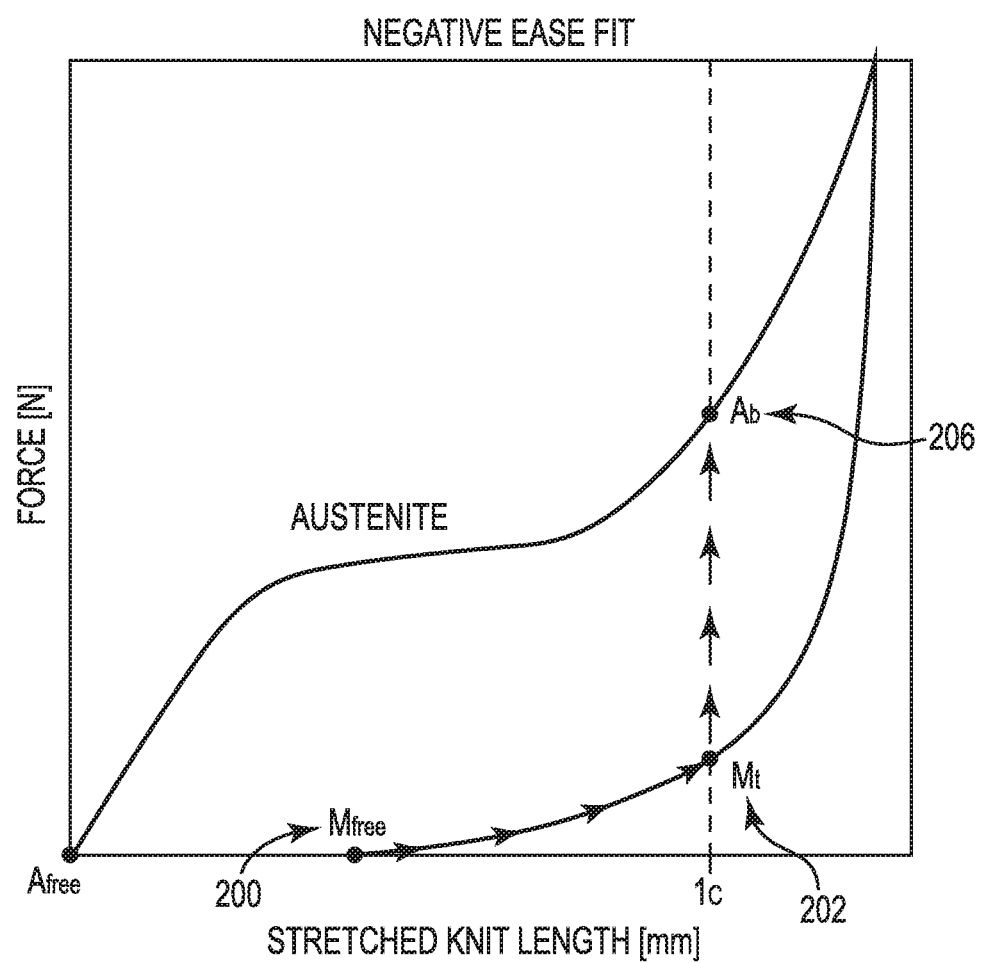
FIG. 2 depicts a force-size diagram of a garment having a shape memory alloy component, according to an embodiment.

Localized fit can be provided by garments that use specific materials and knit patterns disposed about the garment in a pattern to create a desired topography. In particular, the use of shape memory material and specific arrangements of knit patterns can create a topographically-specific garment that ensures good fit between garment and wearer without bridging or loss of contact for sensors or haptic feedback. FIGS. 2 and 3 describe the materials used in such topographically-specific garments, while FIGS. 4-9C describe the arrangements of knit patterns that can create topographical specificity using those materials.

FIG. 2 is a chart of a theoretical model for the force and length of a therapeutic compression garment. Force applied to the fabric or garment, shown on the y axis, can be used to determine a total tension using a tensile test that measures a fabric's tension per unit width (T) at specific lengths, $$T=F/w$$

where the recorded force (F) is divided by the measured fabric width (w). By determining the tension values of the fabric, the pressure exerted by the fabric on a body can be determined for specific body radii. In one example, an orthostatic intolerance lower body garment exerts between about 6 mmHg and about 77 mm Hg (about 800 Pa and about 12 kPa) on the body. The range of fabric tensions required for this garment can be determined using the Hoop Stress formula, Laplace's formula, and Macintyre's formula:

Hoop Stress Formula $$\delta_\theta = F/tw$$

where $\delta_\theta$=hoop stress, F=force in N, t=fabric thickness in m, w=fabric width in meters.

Laplace's Formula $$P=(t\delta_\theta)/r$$

where P=pressure in Pa, t=fabric thickness in m, $\delta_\theta$=hoop stress, r=limb radius in meters.

Macintyre's Modified Formula $$P=(t(F/tw))/r,$$

i.e., P=(F/w)/r, because T=F/w and the t's cancel out;

i.e., $P=T/r$ where P=pressure in Pa, T=fabric tension in N/m, r=limb radius in meters.

Anthropometric data can be gathered to determine the limb radius. The anthropometric data can be specific to a patient, or in embodiments standard or common sizes can be used to generate garments that are appropriate for many wearers. In this example, if the average leg radius is 0.049 meters, Lowest pressure:

$$799.9\ Pa = \frac{T}{0.049\ m},$$

then T=799.9 Pa*0.049 m, then T=39 N/m.
Highest pressure:

$$10265.8\ Pa = \frac{T}{0.049\ m},$$

then T=10265.8 Pa*0.049 m, then T=503 N/m.

So to provide the desired level of compression, the fabric should exhibit tensions levels between 39 and 503 N/m.

Returning to FIG. 2, at 200 the therapeutic garment is an undersized garment in the martensite state. No force is being applied by or to the garment. At 202, some force is applied to the garment to stretch it over the user. The garment remains in the unactivated martensite state, so the length of the garment increases along the bottom curve in FIG. 2 as force is applied to stretch the garment.

At 206, the fabric that makes up the garment is actuated, such as by application of heat. This actuation, or transition from martensite to austenite phase, causes an increase in applied force (i.e., compression), even though there is little to no change in the length of the fabric. The garment size enters a "blocked state" in which it cannot move, but force increases.

The garment can be changed back to martensite to be removed, or in embodiments the state of the fabric can be alternated between austenite and martensite to provide pressure pulses or other therapy, as described in more detail below.

Figure 3A:
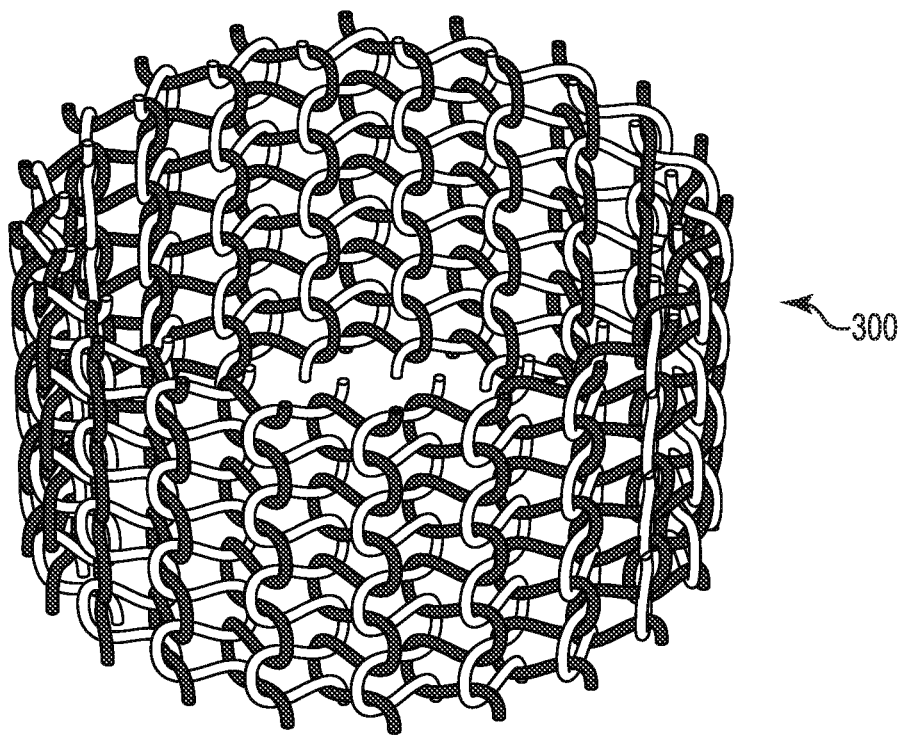
FIGS. 3A and 3B are perspective and sectional views, respectively, of a circular garment according to an embodiment.
Figure 3B:
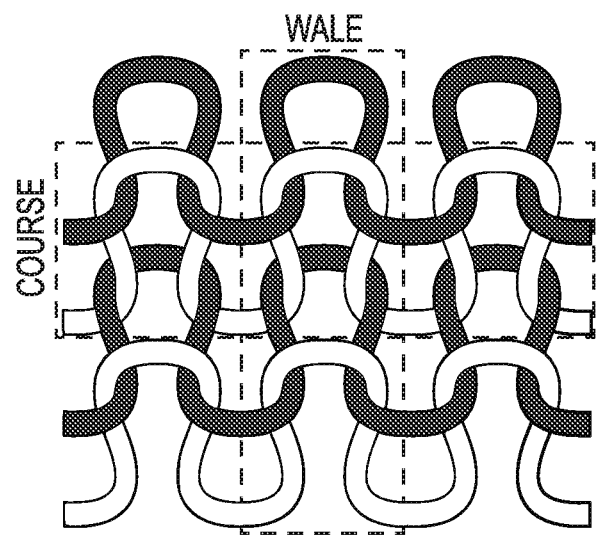

FIG. 3A is a perspective view of an active garment 300, according to an embodiment. As shown in FIG. 3A, interlocked rows and columns (or "courses" and "wales" as shown in FIG. 3B) are arranged in a cylindrical pattern. Knit fabrics are constructed through successively added courses. To achieve circumferential contraction, fabrics are wrapped with courses parallel and wales perpendicular to the length of the body.

Phase transformations can be introduced as a function of the applied materials stress, strain, and temperature, and depend on the thermo-mechanical loading history of the material. The reversible transformation between the cubic austenite and the monoclinic martensite lattices enables variable stiffness, as well as the ability to undergo and recover large deformations of up to 8%, in some embodiments.

Sufficient mechanical straining and stressing of the NiTi-based SMA wire results in a detwinning of the initially twinned monoclinic martensite at temperatures below the martensite finish temperature ($T<M_f$). Upon heating above the material-specific austenite finish temperature ($T>A_f$) the martensitic transformation to the cubic austenite lattices occurs and the imposed strains and stresses are recovered. The initial state of the wire is recovered through subsequent cooling ($T<M_f$) which forces the reverse phase transformation to the original unstructured twinned martensite lattice.

The phase transformation temperatures of NiTi-based SMA are highly programmable and can be tailored for a given application according to chemical composition and metallurgical heat treatment. Spanning martensite start ($M_s$) temperatures between −100° C. and 400° C. while preserving the shape memory effect, NiTi-based SMA renders the potential for a wide array of applications. For binary NiTi alloys, manipulation of the Ni-volume fraction results in drastic variation of the transformation temperatures ($A_f$, $A_s$, $M_s$, $M_f$) and thermal hysteresis. Slight Ni-richness ($c_{Ni}$~51.5 at-%) produces approximately 200° C. lower transformation temperatures compared to marginally Ti-rich ($c_{Ni}$~49%) NiTi-based SMAs. The partial replacement of Ni or Ti with ternary alloying agents modifies the transformation temperatures as a function of the concentration and number of valence electrons. Heat treatment, specifically aging under defined times and thermo-mechanical loads, can cause the formation of precipitates (e.g. $Ni_4Ti_3$) and a consequential increase of the phase transformation temperatures through a decrease of the Ni-content in the matrix.

Figure 3C:
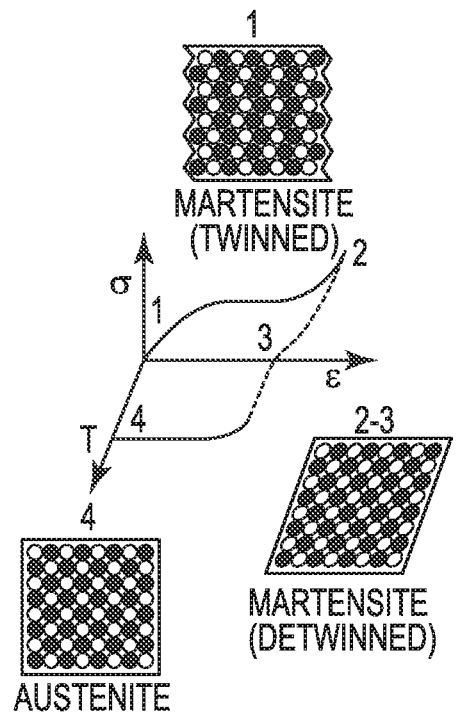
FIGS. 3C and 3D are a phase diagram of a shape memory alloy garment and a force-size diagram of a garment having a shape memory alloy component according to an embodiment.
Figure 3D:
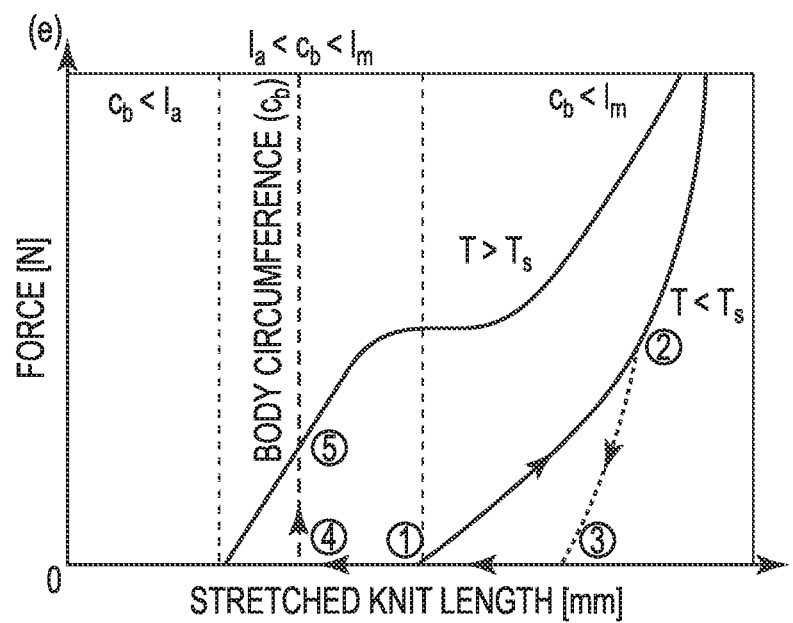

These considerations can be used to develop a garment with appropriate levels of contraction at desired temperatures but, as shown in FIG. 3D, they assume a body circumference that is constant. In reality, most such garments (or indeed other fabrics usable in non-garment applications) will be used on a wearer or object that does not have a set circumference. As shown in FIG. 3D, at the point labeled (1) the garment is in a pre-donned martensite state (PDMS), which is oversized, compliant, and fully martensitic; at (2) the garment is donned and is in a deformed martensitic state (DMS); at the point labeled (3) the garment is in a relaxed martensitic state (RMS) having been donned on the body; at (4) the garment contracts to a fitted, partially austenite state (FPAS), having achieved the dimensions of the body, and at (5) the garment tightens around that form in a tight, partially austenite state (TPAS). Thermal induced martensite occurs as twinned martensite, and the twinned martensite structures turn into detwinned structures by deforming the material in the martensitic condition, as shown in FIG. 3C.

Figure 4A:
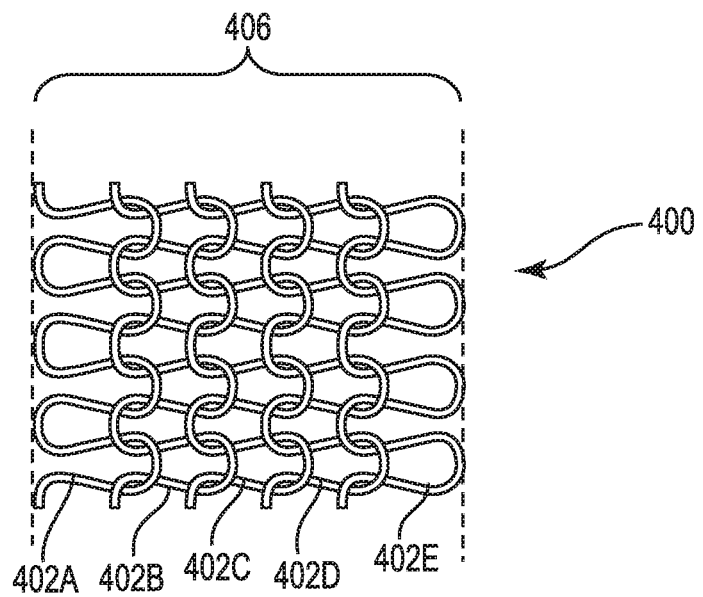
FIGS. 4A and 4B depict unactuated and actuated shape memory filaments, respectively, in a knit pattern.
Figure 4B:
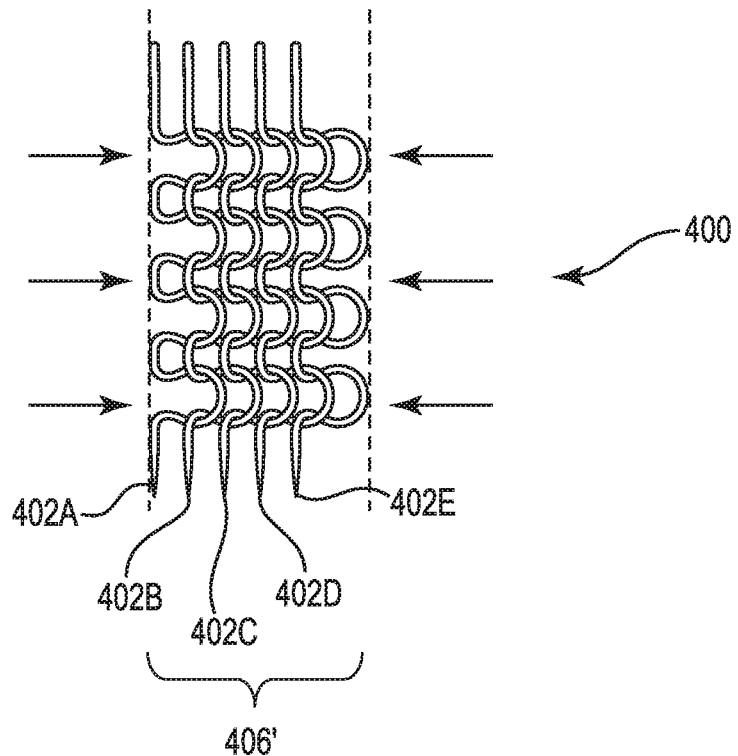

The conversions described above with respect to FIGS. 3A-3D rely on the contraction of interconnected courses and wales to contract the overall fabric or garment, as shown in FIGS. 4A and 4B. FIGS. 4A and 4B are plan views of fabric 400 made of a series of rows of weft knit active yarns in relaxed and contracted states, respectively, according to an embodiment. Fabric 400 includes five rows (402A, 402B, 402C, 402D, 402E) of an active yarn material. The term "active yarn material" can refer to any thread, strand, filament, braid, or bundle of materials that responds to thermal or electrical stimulation to change from a relaxed state to an activated state. In embodiments, braided or coaxial bundles can provide a relatively higher level of strength than individual filaments and can also provide more force when switching between relaxed and activated states.

The active yarn material that makes up each of the rows 402A, 402B, 402C, 402D, 402E can comprise a shape memory alloy (SMA). In embodiments, the SMA can be a type of active metal with shape memory properties that is highly malleable in a cool, martensite phase and has shape recovery abilities, even under load, during the elastic austenite phase. In one embodiment, the active yarn material can be a nitinol material. SMAs can be engineered to switch from martensite to austenite depending on whether they are above or below a material-specific transition temperature.

SMAs can be engineered to exhibit desired properties by altering the material composition and the heat treatments. Specifically, stress, strain, recovery, and activation temperature are functional properties that can be manipulated through the thermomechanical manufacturing process. Consequently, SMAs can be designed to activate at specific temperatures to require relatively low power consumption (or no-power consumption in the case of body-heat actuated nitinol chemistries) and temperature loads on the body compared to powered, pneumatic systems.

Knit structures such as fabric 400 can be used in large, complex structures that are actuated across complex surfaces (such as the surface of the body). The variety of structures that can be created with interlocking loops or stitches within each row (e.g., rows 402A, 402B, 402C, 402D, 402E) and the shape change that occurs when these loops are subject to tension can be customized to the contours of a particular body part such as a leg or arm.

Knitting can be divided into two general architectures: (1) weft knitting, which is a process in which an individual end of yarn is fed into or knit by one or more needles in a crosswise (lateral) fashion, and (2) warp knitting, which is a process in which a multiplicity of yarns are fed into or knit by one or more needles in a lengthwise (vertical) fashion. While weft knits have more mechanical stretch, warp knits are often more stable architectures and can be constructed using many wales, or columns, of yarn. Additional yarns can be introduced into weft knit structure by utilizing a jacquard system, which selectively engages and disengages needle beds to form a knit pattern using multiple yarns. Warp knits can also achieve complex patterning through the use of guide bars, which allow some warp knit structures (e.g., raschel knits) to appear like lace-structures. Hand-knitting (a weft knit structure), lace-making, crocheting, tatting, and needle-lace are other manual methods of selectively looping yarns into a fabric structure. Complex patterns can be achieved using other techniques such as hand-knitting, lace-making techniques, or others, which can be used to loop yarns selectively into the fabric structure. Although FIGS. 4A and 4B depict a simple weft pattern, other embodiments can include a variety of relatively more complex knitting stitches and patterns including warp knitting, jacquard, intarsia, Fair Isle, or any other knitting pattern and combinations thereof.

FIG. 4B shows the same five rows 402A, 402B, 402C, 402D, 402E of active material described above with respect to FIG. 4A, but in FIG. 4B the rows 402A, 402B, 402C, 402D, 402E are in a compressed state indicated by arrows. Fabric 400 can change from the relaxed state shown in FIG. 4A to the compressed state shown in FIG. 4B due to a change in temperature. For example, the active material can have a transition temperature, and once each of the rows 402A, 402B, 402C, 402D, 402E becomes hotter than that transition temperature the active material can transition from martensite to austenite, and vice versa.

As shown in FIGS. 4A and 4B, depending upon the state of the rows of an active material, the overall width of the fabric can vary. Width of an active fabric can be relatively wider in the relaxed state, and relatively narrower in the activated state. A user can change between these two states by heating or cooling the rows. To heat the rows, electrical current can be routed through some or all of the rows. Alternatively, an adjacent liner can provide heat or cooling to fabric to cause it to change between activated and relaxed states.

A fabric made of a shape memory alloy or other active knit material can be modified to form other fabric types or patterns by changing any of at least six features. First, the relative number of active yarns to passive threads can be varied to provide different levels and targeted areas of compression. Second, the stitch size or relative density (i.e., gauge) of the stitches can be modified to affect the knit index $i_k$. Third, current and voltage (or power dissipation) through the active yarns can be controlled to affect activation of the active textile or electrically-isolated regions of the knitted garment. Fourth, the weight or diameter of the yarn (which can be either a single filament or a bundle of active filaments) can be modified, with thicker yarns generally providing a higher level of compression upon activation. Fifth, the transition temperature of the active yarns can vary between embodiments, and in fact within segments of the same fabric, to create zones as described in more detail below. Zones that have different transition temperatures will activate at different times, even under uniform heating or cooling. Finally, structural strain of the fabric (martensite) can be increased to produce much larger actuated compressive pressure.

It should be understood that different courses and wales can be made of different materials, which can be combinations of various shape-memory or superelastic materials, and which can also include passive materials. The combinations of materials used therein can create desired contraction patterns when the materials are activated.

Figure 5:
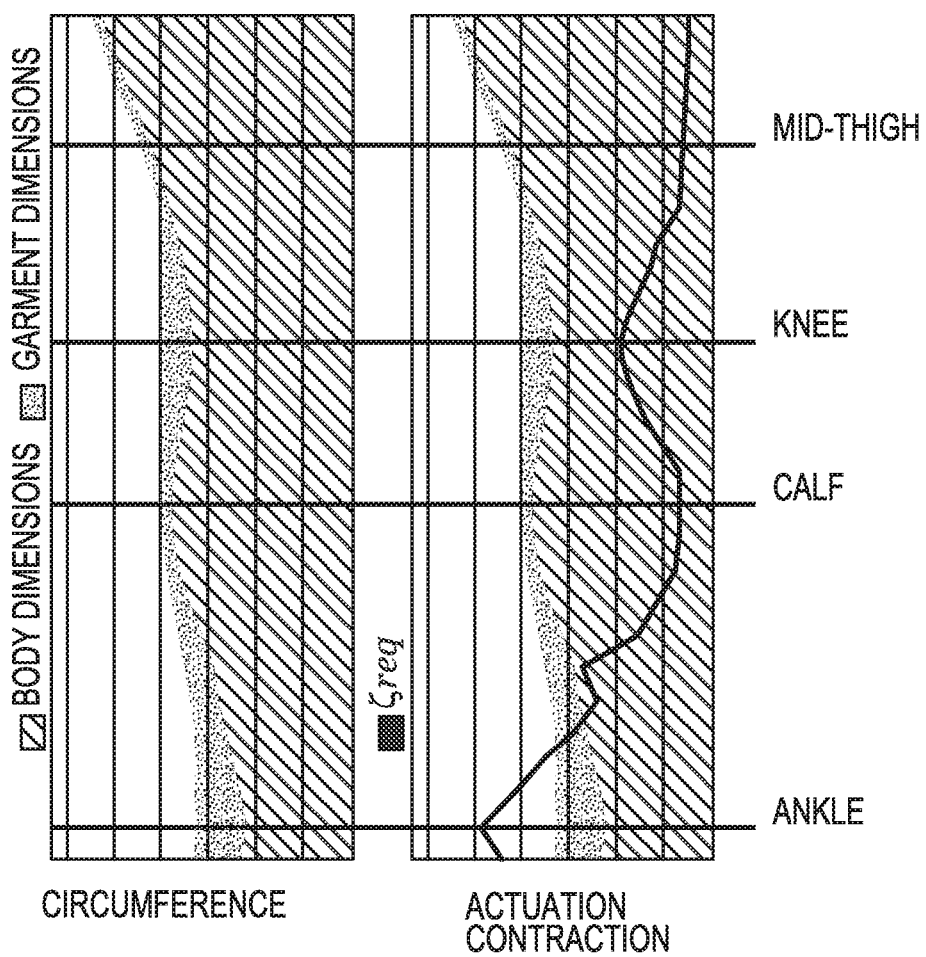
FIG. 5 depicts the circumference of a user's leg, corresponding garment dimensions, and required garment actuation contraction according to an embodiment.

In addition, as shown in FIG. 5, a self-fitting garment can be designed by mapping the body-garment relationship. Contractile SMA knitted actuators exhibit tunable functional performance through the systematic modification of geometric design parameters, specifically wire diameter d and knit index $i_k$, as described above. Before determining suitable knit geometries to achieve self-fit, the body-garment relationship can be mapped. Mapping can be accomplished by gathering dimensional data from a sample group. Marks can be placed on the participants' body and at each incremental mark, a circumferential measurement is taken.

Once circumferential measurements have been gathered, the performance requirements of the self-fitting garment can be compared with the measurements to design a garment. For an inextensible garment, the minimum garment dimension required at the base of a pant leg to enable don/doff (i.e., traverse the foot) was determined to be the calf dimension plus 2.5 cm of positive ease. This recommended added garment dimension means that the garment circumference around the ankle should be equal to the garment dimension around the calf. Additionally, the garment dimension around the knee for an inextensible garment must be equal to the garment dimensions around the calf to enable the garment to traverse the calf. The required functional performance of the self-fitting garment is consequently defined as the percentage difference between the garment dimensions and the body dimensions. The circumference of the body and the garment are shown in the left-hand side of the graph in FIG. 5. Based on the initial and desired contracted circumference at each portion on the body (i.e., the initial length and contracted length of each circumferentially-extending shape memory coil), the required contraction $\zeta_{req}$ can be determined.

For garments that are designed primary for comfort and aesthetics (i.e., where desired compression is near zero rather than a positive value), actuation contraction $\zeta_{req}$ should ordinarily be maximized while the force applied $F_{app}$ should be minimized, while still maintaining desired contraction under forces that are to be expected during wear.

Figure 6A:
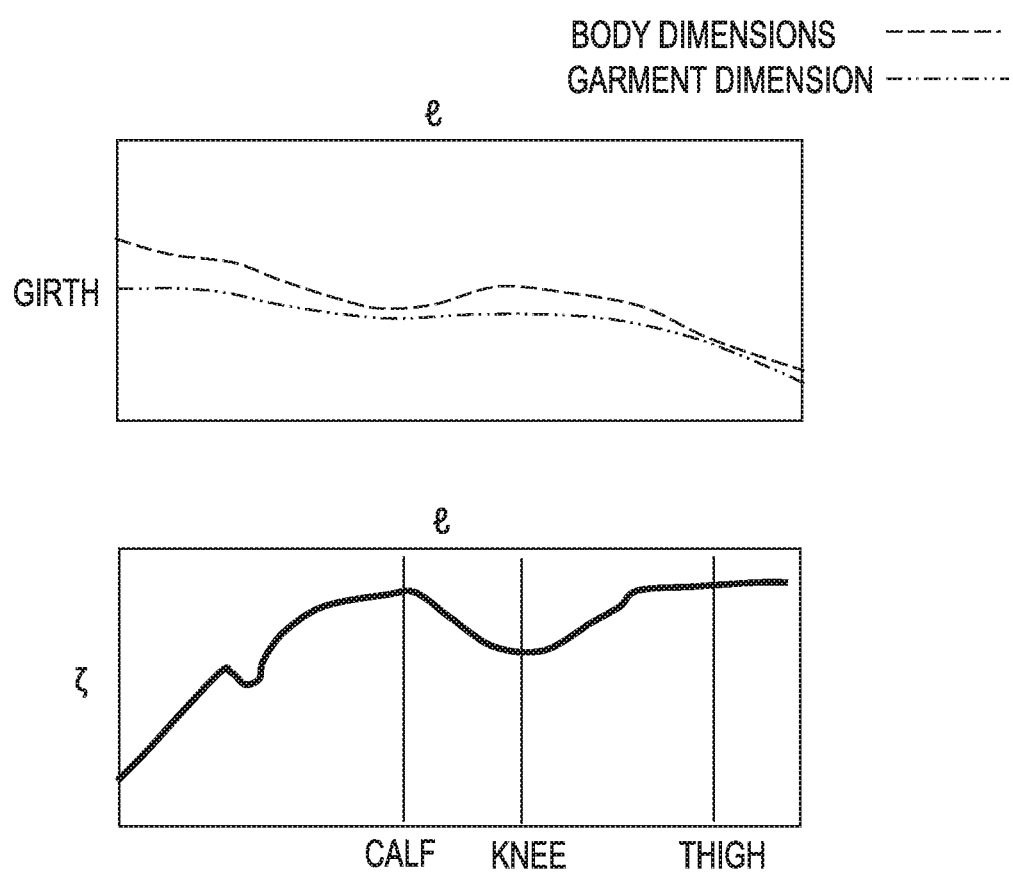
FIGS. 6A-6D depict a garment having sections with different contraction levels corresponding to actuation contraction requirements based on the wearer's body dimensions according to an embodiment.

An extensible, active fabric garment that improves upon these characteristics is shown in FIGS. 6A-6D. The garment dimensions and body dimensions shown in FIG. 6A are roughly paired with one another, for a typical human leg.

Uniaxial contraction is accomplished upon heating above the austenite finish temperature through the recovery of bending deformations and formation of ridges between alternating courses of knit and purl loops, which are mirrored opposites. As described above, the %-actuation contraction ($\zeta$) of SMA knitted actuators is defined as $\xi=(l_m-l_a)/l_m$ the normalized difference between the fabric's martensite length ($l_m$) and austenite length ($l_a$) at a given load and, while following the engineering strain definition, named in clear distinction to material strains. The complex thermo-mechanical loading state of SMA knitted actuators with variable strains and stresses inhibits the assumption of full austenitic transformation at $A_f$, which is defined as a stress-free transformation temperature. The dimensions of a participant's leg collected for the design shown in FIG. 6A are plotted along with the minimum garment dimensions to enable don/doff, specifically to pull the garment over the heel. Similarly, the design requirements for a wrist sleeve can be determined by plotting the body dimensions along with the minimum garment dimensions to enable the sleeve to be pulled over the maximum hand circumference, or other similar calculations can be performed based on the anatomical features of the wearer for other garments.

Figure 6B:
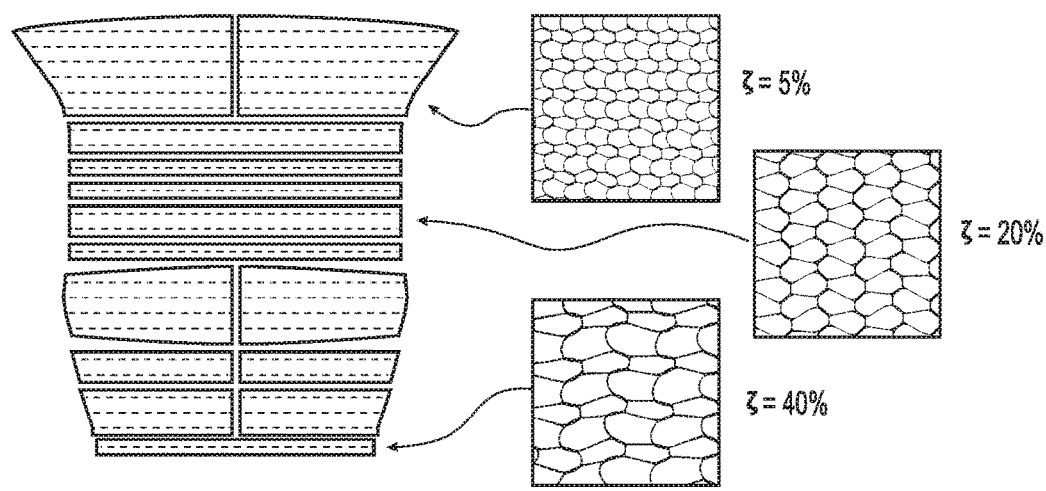

As shown in FIG. 6B, various sections of differently knitted patterns can be formed that cause appropriate levels of contraction to provide a desired level of compression at each part of the leg. $\zeta_{req}$ may be between about 5% and about 40% in this embodiment, though it should be understood that depending upon the minimum garment dimensions to enable donning and the type of anatomy of structure that the fabric is compressing, $\zeta_{req}$ could vary widely. The curves shown in FIG. 6B show that self-fitting garments should have a functionally graded design to prevent over-constricting certain areas of the body (e.g., thigh) and under-fitting others (e.g., ankle). Comfort requirements were established to retain garment pressures below that of medical compression garments. The critical force ($F_{crit}$) at which the critical pressure is reached ($p_{crit}$=1300 Pa) was determined for the variable limb cross-sectional radius (r) per standard cross-sectional fabric width (w=0.02 m), assuming rigid cylinders.

The twenty-four dashed lines in FIG. 6B each represent a corresponding circumferential measurement taken around a participant's leg in 2 cm increments. Dark outlines represent the boundaries of knitted panels, composed of a group of adjacent circumferences that require the same fabric actuation contraction behavior for fitting. These sections can be connected via directly knitting together those sections, or alternatively they can be coupled to one another via some other form of connecting stitch such as those described below with respect to FIGS. 13 and 14, among others. The details of each SMA knitted actuator paired with each knit panel, specifically wire diameter (d) and knit index ($i_k$), are indicated on the expanded boxes on the right-hand side of the drawing.

Figure 6C:
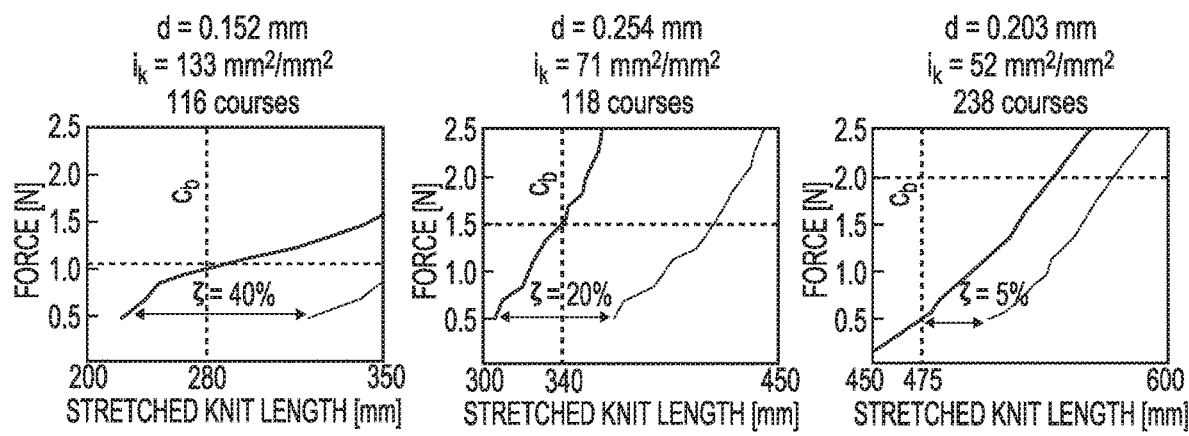
Figure 6D:
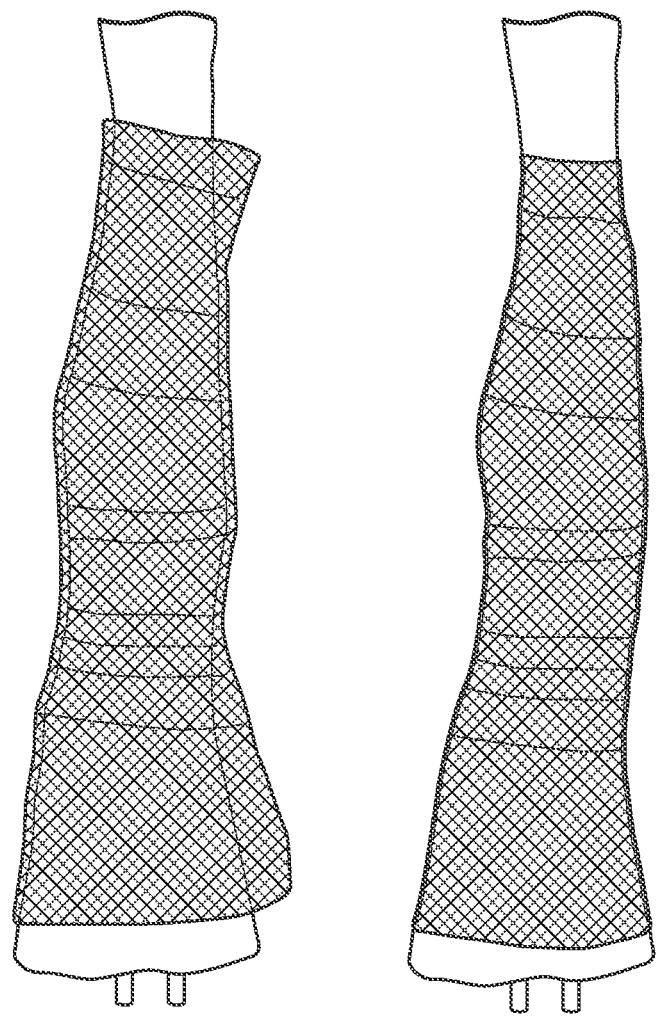

Force-length plots are shown in FIG. 6C. Force-length plots will vary by body circumference ($c_b$). Garment pattern dimensions can therefore be determined by pairing body circumference ($c_b$) measurements with the appropriate SMA knitted actuator force-displacement curves as shown in FIG. 6C. Knitted courses were added or subtracted to position the body circumference ($c_b$) between the austenite knit length ($l_a$) and martensite knit length ($l_m$) to keep forces below 10 mmHg. In FIG. 6D, the completed self-fitting garment is depicted in unactuated (left) and actuated (right) states.

An innovative approach towards a quantitative measure of fit (traditionally a qualitative process) was developed through three-dimensional, non-contact displacement and strain measurements from 3D marker tracking. The experimental validation methods were designed to measure the success of the self-fitting design by (1) assessing the fit quality through comparison of the fitted garment dimensions in relation to the dimensions of the participant's leg geometry, and by (2) characterizing the accomplished %-actuation contractions in the fitting process.

Figure 7A:
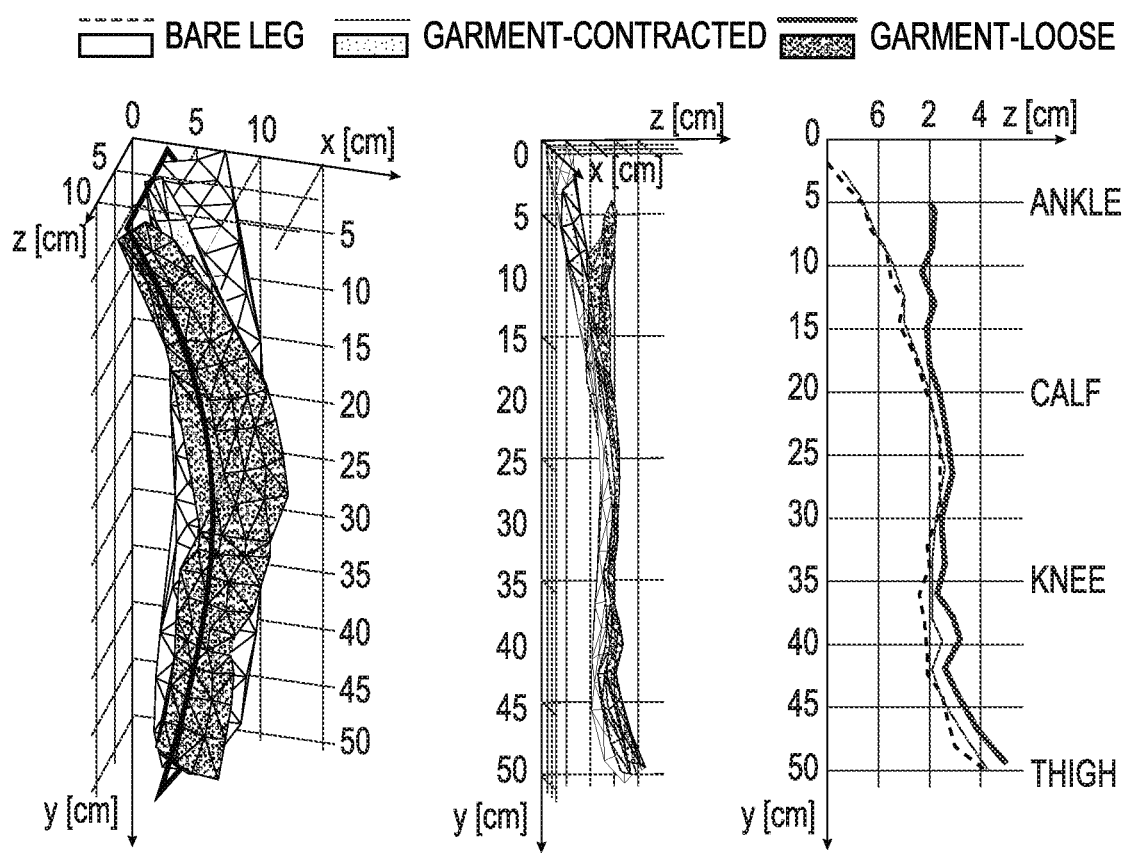
FIGS. 7A-7C depict three-dimensional fit of a garment on a user's leg according to an embodiment that uses 3D image tracking.
Figure 7B:
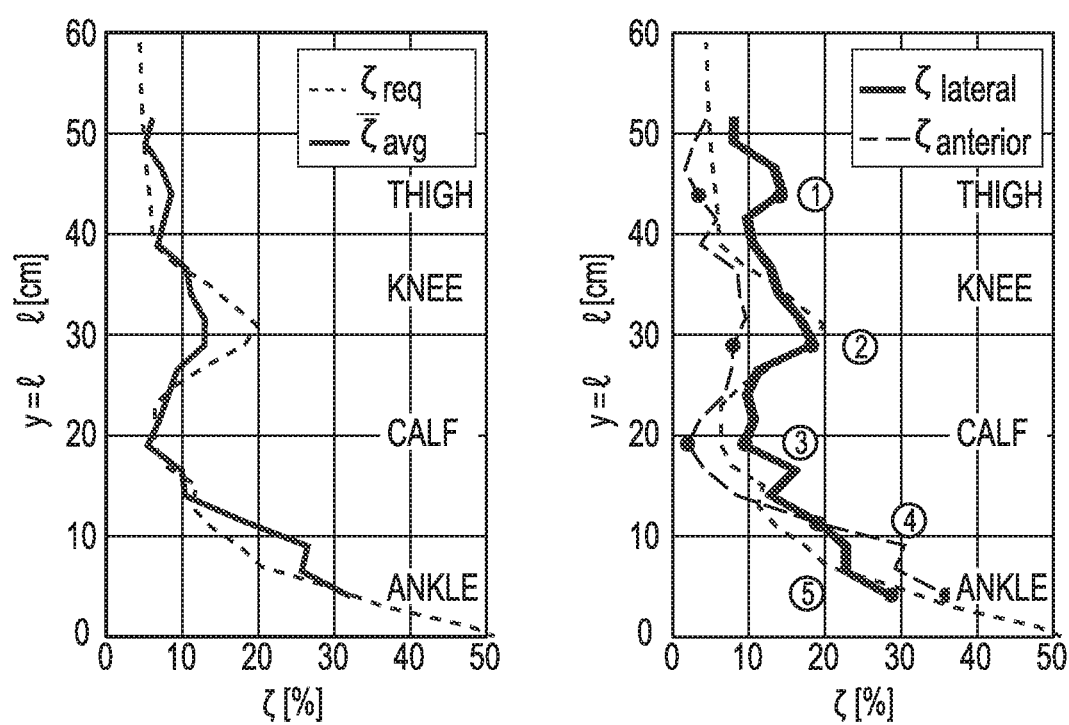
Figure 7C:
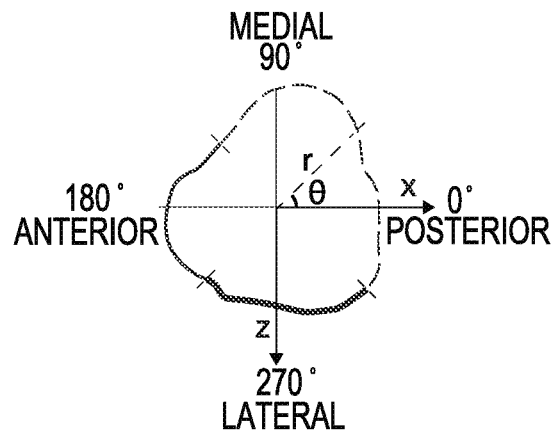
Figure 7C:
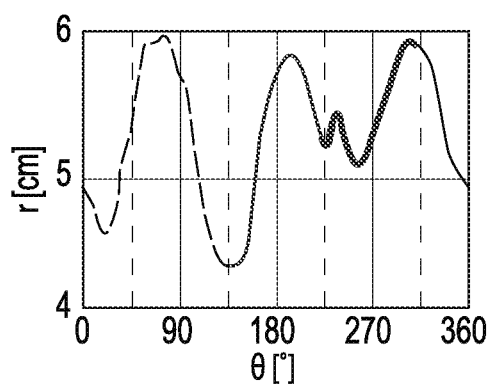
Figure 7C:
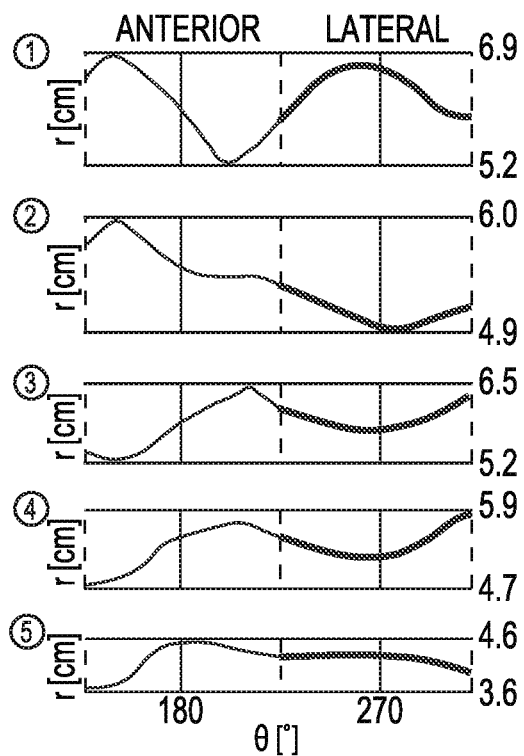

As shown in FIGS. 7A-7C, in addition to garment-body proximity, 3D marker tracking data can be used to evaluate garment actuation contraction and shows garment over-contraction in some areas of the body and under-contraction in others. FIG. 7B displays the average %-actuation contractions ($\zeta_{avg}$) derived from the normalized difference of Euclidean distances between neighboring markers based on size differences between the garment and leg in loose and contracted states, respectively, as depicted in FIG. 7A. Measurements towards the ankle (y=5-15 cm) depict average overperformance caused by a larger than predicted martensite garment dimension. In contrast, measurements at the knee (y=31 cm) depict average under-contraction of up to 7 percentage points. FIG. 7B on the right-hand side splits the anterior and lateral views to show that, while the self-fitting marker measurements above the ankle (y=11-46 cm) show under-contraction in the anterior view, over-contraction occurs in the lateral view. Only lower calf cross-sectional areas (y=10.2 cm), which are approximately cylindrical, show identical %-actuation contraction in both lateral and anterior views, suggesting performance is dependent on the surface topography upon which contractile SMA knitted actuator fabrics actuate. The consistent under-contraction of the self-fitting garment around the knee, specifically at y=32 cm where both lateral and anterior views under-contract, could motivate further changes to the knit pattern, knit index, fiber thickness, or materials used in the garment to result in uniform contraction. In embodiments, models or experimental data can be used to improve or iteratively adjust garment designs like the one shown in FIG. 7 to result in a garment having a desired level of uniformity of compression.

A self-fitting garment can contract fully and not be proximal to body concavities just as the garment can be proximal to the body and not fully contracted across body convexities; therefore, the quantitative analysis can be supplemented with a topographical analysis to demonstrate the effect of non-cylindrical body shape on purely contractile SMA knitted actuators. As depicted in FIG. 7C, each cross-section was divided into medial, lateral, anterior, and posterior quadrants. The equivalent radial coordinate (r) of each cross-section was analyzed with respect to the angular coordinate ($\theta$). Five spliced lateral and anterior radial coordinate plots chosen as extreme examples were then matched with the %-actuation contraction performance plots in FIG. 7C. Comparing FIGS. 7B and 7C, areas of topographical concavity or relatively mild convexity contracted adequately, while garment under-contraction occurred at angles of extreme topographical convexity. Here concavity and convexity are defined analogous to convex functions. If a line segment between any two $r(\theta 1)$ and $r(\theta 2)$ is consistently equal or greater than the values of $r(\theta)$ between $\theta 1$ and $\theta 2$, the topography is called concave. Extreme concavities are those concavities that maximize the area enclosed by the line segment and $r(\theta)$. Topographical convexities follow the same definition for $-r(\theta)$.

In general, regions are referred to as being "concave" if the intermediate radius is less than the surrounding radii by some threshold. The threshold can be determined by a designer based on the desired level of compression, the materials being used, and how important the level of fit is. Depending upon the embodiment, the threshold can be defined either by a total change in size or shape. In one embodiment in which topography is measured by change in radius about a central axis, a designer can choose an appropriate threshold "x" to define regions within the garment as follows:

$$\text{Concave: } \frac{\partial^2 \theta}{\partial r^2} > x$$

$$\text{Flat: } -x > \frac{\partial^2 \theta}{\partial r^2} > x$$

$$\text{Convex: } \frac{\partial^2 \theta}{\partial r^2} < -x$$

In another embodiment, a radius change (in relation to a body center) or distance change (in relation to an anatomical plane) between an intermediate radius and surrounding radii of 1 cm or more requires the design strategy for concavities. A radius change less than 1 cm could benefit from a topographically conforming fabric if that radius/distance change occurs between datapoints spaced less than 3 cm apart. For example, the hand may exhibit small changes in distance from the coronal place around the knuckles (<1 cm), but the change in distance (topography change) is so compact/abrupt that topographically conforming fabrics could be needed based on tightly spaced measurements. In other embodiments the topography can be evaluated in terms in distance from an anatomical plane. For example, the hand topography would be best quantified in terms of distance from the coronal plane because the hand is a long and narrow shape rather than a substantially cylindrical shape.

To improve the fit of SMA knitted actuators, specifically to conform around body topography, modified grid patterns can be used to achieve fully spatial actuation for a variety of body cross-sections between the knee and thigh (y=32 cm, FIG. 7B). This part of the body was chosen as an example because of its complex geometry. The cross-section was 3D printed and three variable grid pattern prototypes were manufactured. The results of these trials are shown and described with respect to FIGS. 8A-8C.

FIGS. 8A-8C show a fabric with a knit pattern for both concave and convex elements in the cross-section, as defined above with respect to FIGS. 7A-7C. FIG. 8A is a perspective view of such a garment 800. FIGS. 8A-8C depict an iterative and improving process for forming a garment that provides uniform compression across a cross-section including both convex and concave sections. As shown in the progression from FIG. 8A to FIG. 8B and then FIG. 8C, the garments are a combination of garter, purl, and knit sections and by including appropriate segments of each type of pattern an overall topography can be created that is more attuned to the specific cross-sectional shape of the body.

As shown in FIGS. 8B-8C, in section 1 of each drawing, a garment 801 made entirely of garter stitch is arranged around the wearer W (or in this case the 3D-printed model). The resulting contact level between garment and wearer is about 70%, as the contracted garment bridges over concave sections of the anatomy of the wearer W.

Garment 802 in section 2 is a modified version of garment 801, in which garter knit sections have been replaced by purl or knit sections to selectively shape the garment 802. By using these sections selectively to match with the user's anatomy, the amount of contact with concave surfaces between wearer W and garment 802 is increased. However, transitions between the three different architectures produce areas that lift off the surface and create "fluttering contact" with less pressure applied, such that the total surface area with good contact is reduced to 54%. "Good contact" in this case is defined as providing 100% of the desired compression level, "fluttering contact" is 50% or more of the desired compression level, and "no contact" is less than 50% of the desired compression level. Alternatively, the goodness of fit can be measured using force sensing, rather than contact sensing.

Garment 803 is a design that is still further refined from garment 802, with smaller and more targeted use of garter, knit, and purl sections to create a garment 803 that more closely mimics and accurately contacts the wearer W when actuated (86% contact).

Figure 9A:
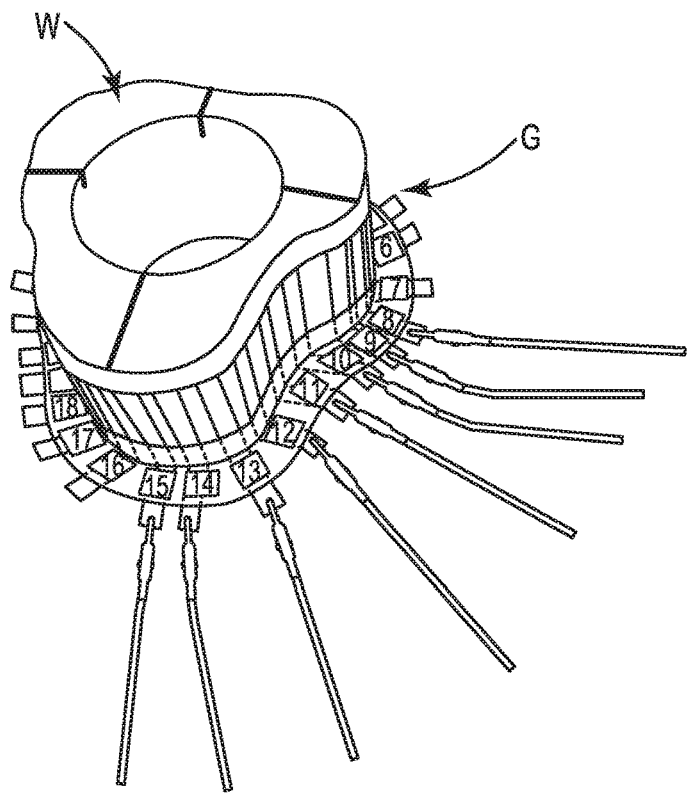
FIGS. 9A-9C depict a testing mechanism for determining the contact between a non-cylindrical, topographically-complex body segment and a garment, according to an embodiment.
Figure 9B:
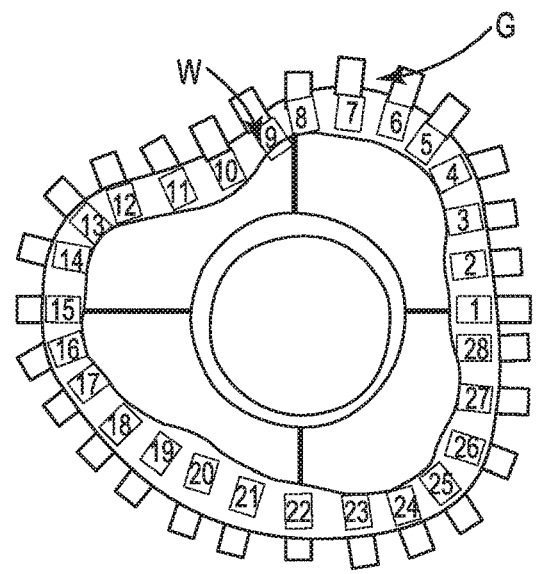
Figure 9C:
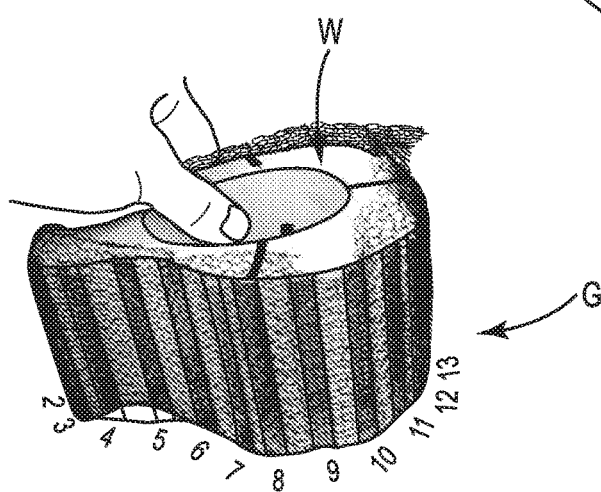

FIGS. 9A-9C are perspective, top, and photographic views of a system for measuring garment-body contact, respectively, according to an embodiment. Each of the indices 1-28 is configured to detect discrete points of contact on a wearer W when the garment G is actuated. Sensors corresponding to each discrete contact point (1-28) can include any electrically-conductive material. In other embodiments, force-sensing methods could be used to characterize the compressive pressure of a garment with force sensors, such as piezoelectric materials, capacitive sensors, spring force sensors, or any other sensing mechanism for pressure or displacement. Strain sensors (contact or non-contact) could also be used to calculate garment compression by relating changes in fabric tension around a given body circumference. From this data, a method for forming a garment can be created, as depicted in FIG. 10.

Figure 10:
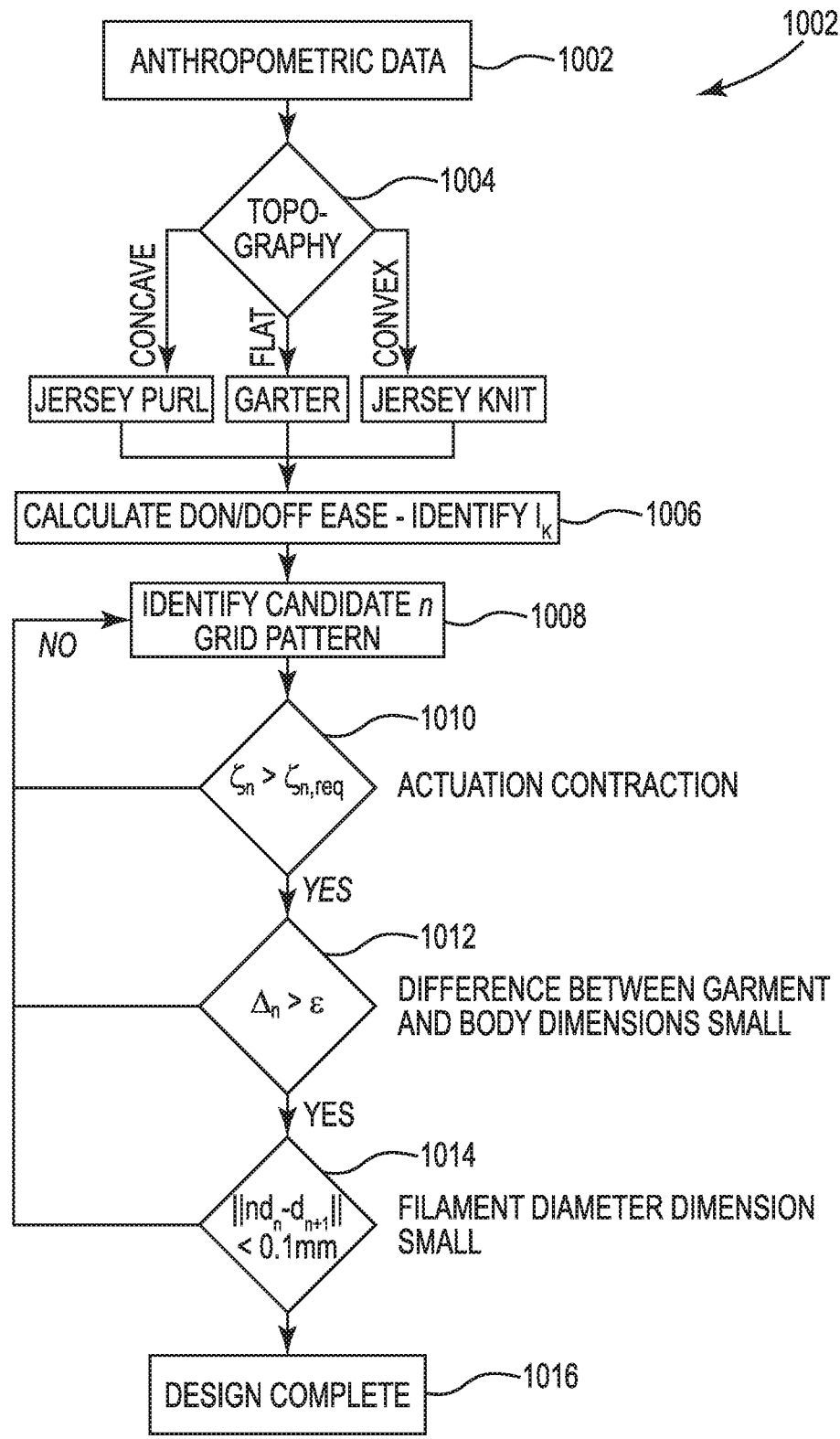
FIG. 10 is a flowchart describing the iterative process by which a self-fitting garment with incorporated grid pattern is created, according to an embodiment.

In FIG. 10, a method 1000 of forming a garment topography is shown. Method 1000 includes collecting anthropometric data at 1002, which forms the basis of the garment design. With respect to the embodiment in FIGS. 9A-9C, for example, anthropometric data 1002 would include the shape of wearer W.

At 1004, a determination is made of the topography of the anthropometric data, and in particular whether each section thereof is concave, flat, or convex as defined above. In the case where the topography is primarily concave, jersey purl (reverse of jersey knit) is used; in the case where the topography is mostly flat, garter is used; and in the case where the topography is mostly convex, jersey knit is used. This is shown as the first iteration at FIG. 8, section 1, for example, in which an all-garter-knit design was used.

At 1006, $i_k$ is calculated to determine the ease of donning and doffing. Based on this calculation, a candidate grid pattern (i.e. combination of knit patterns) is set at 1008. Ease of donning or doffing can be calculated based on a level of force or pressure applied to the anatomy upon donning or doffing, for example. For low-force (self-fitting) garments, the donning/doffing force can be maintained between 0-5 N depending upon the garment. Reductions in force can be accomplished in the initial grid pattern by increasing the physical dimensions of the garment (i.e., creating positive ease) such that any circumferential dimension is 1 cm larger than the largest body circumference the garment must pass over. That is, for a self-fitting, no-closure device:

$$l_g = l_b + (l_{b,max} - l_b) + 1$$

where $l_g$ is the length/circumference of the garment, $l_b$ is the length/circumference of any body cross-section, $l_{b,max}$ is the length/circumference of the maximum body cross-section that the former body cross-section must pass over, and 1 is the 1 cm added ease.

Figure 15A:
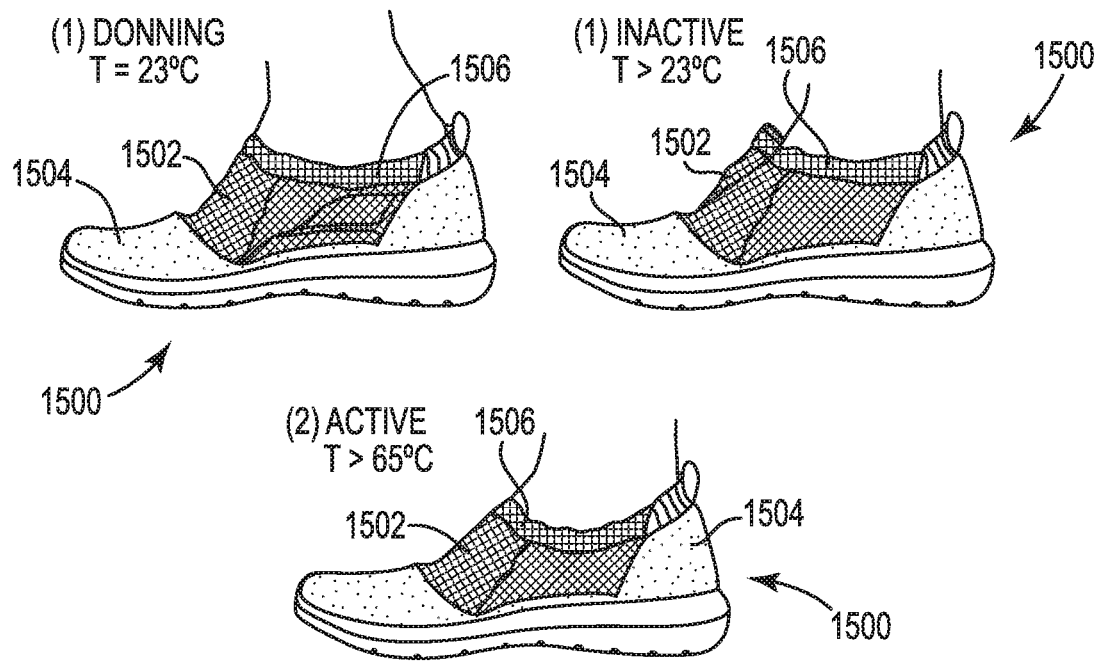
FIG. 15A-C shows an example of an embodiment of footwear incorporating shape memory elements and connecting sections to form a garment that is topographically conforming.

For two particular examples, the leg sleeve of FIG. 6D and the shoe of FIG. 15A, the donning/doffing ease can be determined by the heel circumference+1 cm. For arm devices, the donning/doffing ease is determined by the circumference of the hand+1 cm. For chest/neck devices, the donning/doffing ease is determined by the circumference of the head+1 cm. The positive ease measurements can be reduced with the addition of a closure mechanism, such as zipper, laces, snaps, or hook and loop tape. These mechanisms can reduce donning/doffing ease to 1 cm and donning/doffing force would still be within the 0-5 N range.

For embodiments of self-fitting garments including a closure, the equation can be adjusted to:

$$L_g = l_b \pm 1.$$

For high force (compression) garments, the force can be up to 30-40 N at peak force during donning or doffing. This value corresponds to the maximum donning force experienced wearing conventional medical compression garments on the market. These garments are often deigned with negative ease, meaning that the inactive garment dimensions are smaller than the body dimensions.

$$L_g < l_b$$

Consequently, donning force ($F_d$) is a function of fabric strain ($\varepsilon$) and the inactive actuator stiffness (k)

$$F_d = f(\varepsilon, k)$$

In general, fabrics with higher strain and larger inactive stiffness will require a larger donning force and fabrics with lower strain and smaller inactive stiffness will require a smaller donning force. To reduce donning force as the garment is pulled around the body, closure mechanisms can be used to prevent the garment from having to be pulled over regions of the body. For example, a zipper could be added to the ankle region to allow the garment to expand as it passes over the ankle circumference.

Based on the initial grid pattern that is calculated, actuation contraction (1010), critical force (1012), and filament diameter difference (1014) are considered. If the actuation contraction is less than $\zeta_{req}$, or if the blocked force is greater than $F_{crit}$ or if the filament diameter difference is too great, then a new and updated grid pattern is determined at 1008. In some cases, a new grid pattern may not be required, but the number of total loops in each grid patterns may be modified to (1) improve donning and/or decrease compressive forces by making the inactive garment larger through increased courses of knitted loops and (2) increase compressive forces by making the inactive garment smaller through decreasing courses of knitted loops. Otherwise, once all the requirements for an acceptable garment that provides adequate compression at all regions of the wearer and can be easily donned and doffed is finalized at 1016.

Figure 11A:
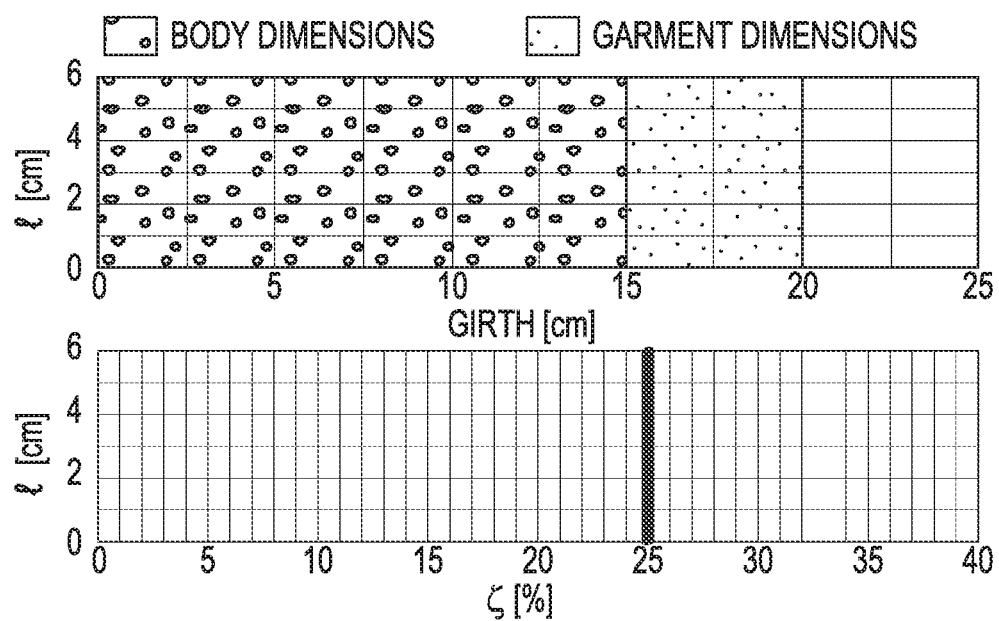
FIGS. 11A-11C depict a garment having a relatively more complex pattern than the garment of FIGS. 8A-8C, while maintaining desired levels of compression across the garment, according to an embodiment.
Figure 11B:
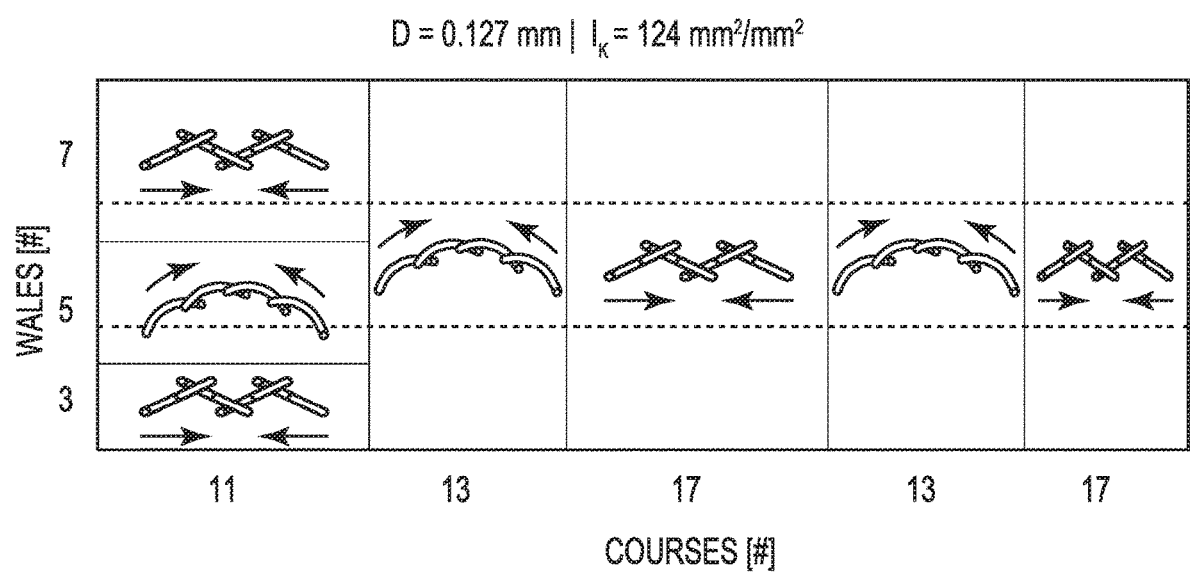
Figure 11C:
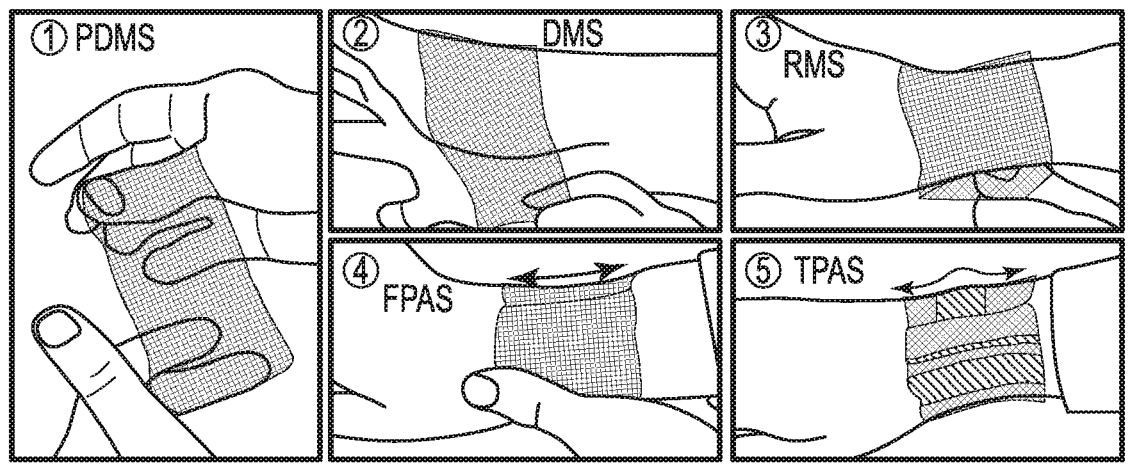
Figure 11C:
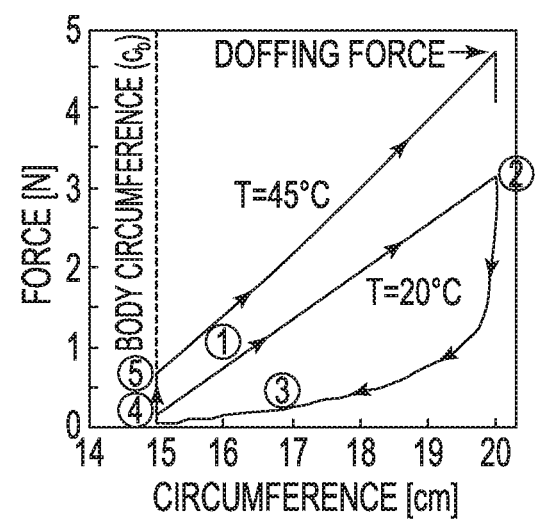

An example of a garment for a more complex geometry is shown in FIGS. 11A-11C. In particular, FIGS. 11A-11C depict a garment for a wrist, which includes concave, convex, and flat features. As shown in FIG. 11B, the wales and courses are varied between knit types to create zones of knit and garter patterned to mimic the contours of the wrist and promote even application of garment-body contact when actuated. In other embodiments, improved garment-body contact produces improved compression around the body.

Figure 12:
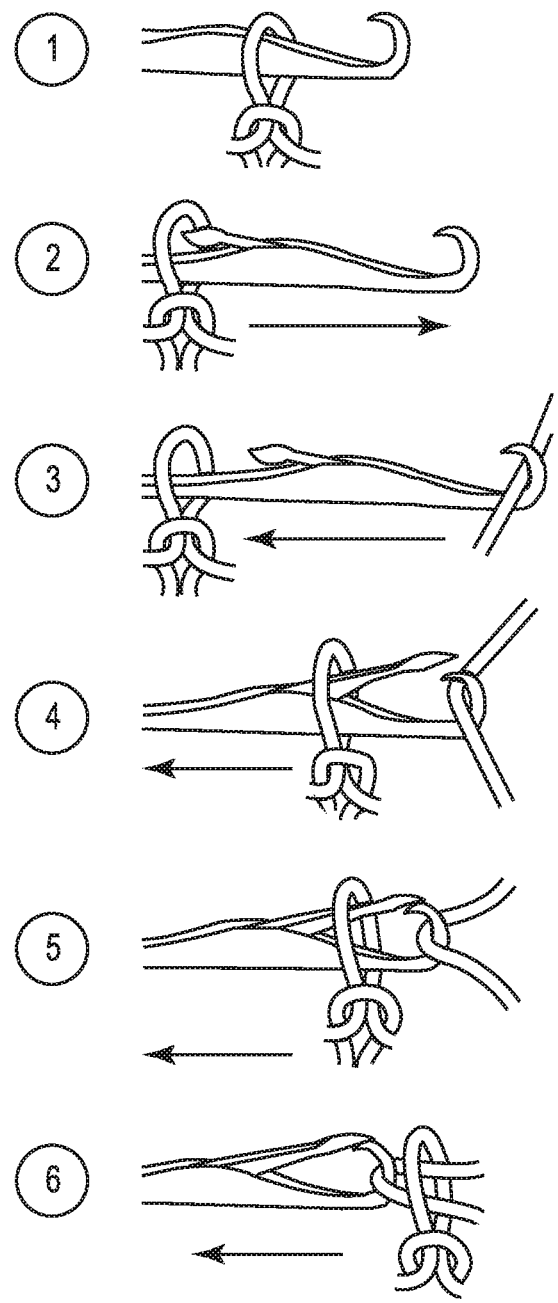
FIG. 12 depicts a latch needle that can be used to form traditional weft knit textile loops to form embodiment garments.
Figure 13:
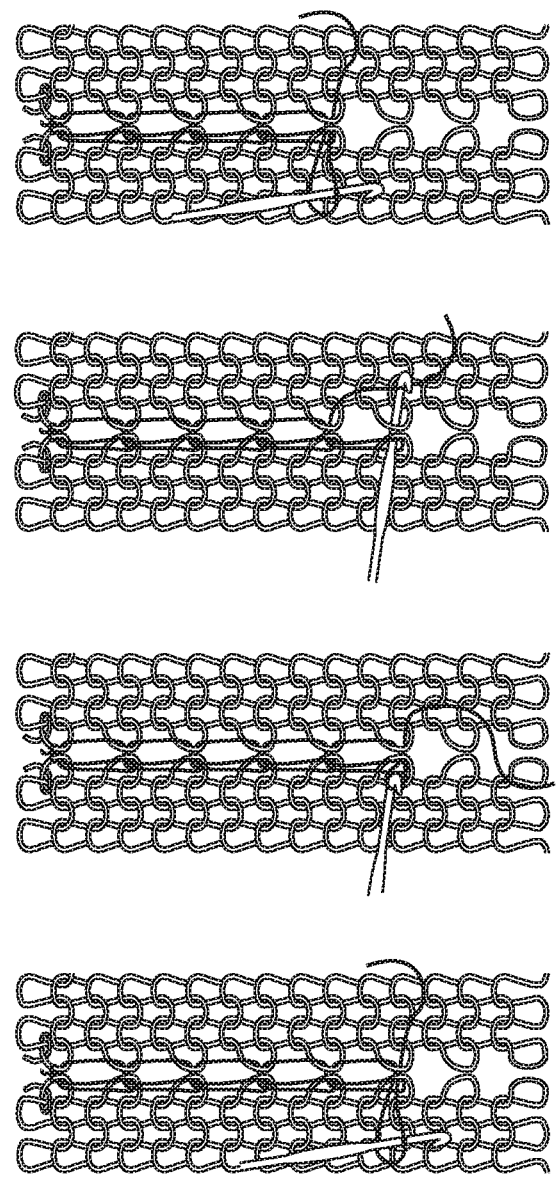
FIG. 13 depicts a crochet connection between two panels of active fabric, according to an embodiment.
Figure 14:
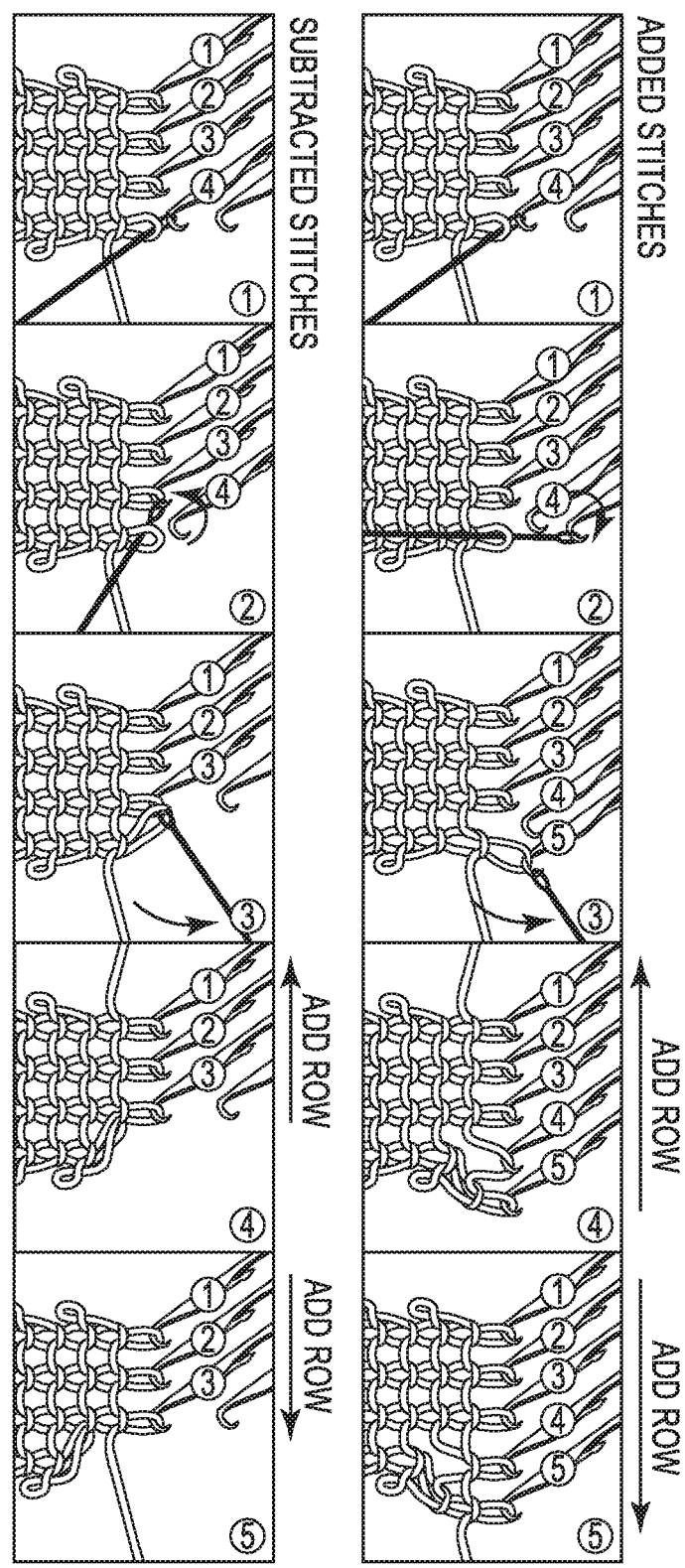
FIG. 14 depicts a process of knit shaping, according to an embodiment.

FIG. 12 is a flowchart depicting the six steps of forming interlocking loops with a flatbed knitting machine. Flatbed knitting machines can be used, in embodiments, to insert panels of active fabric within a broader garment. FIG. 13 depicts a crochet stitch that can be used to join an SMA knitted actuator panel to the remainder of a garment. The crochet hook, holding the filament loop, passes through a knitted loop at the ends of adjacent knit panels. The crochet hook catches the end of the free filament and pulls the filament through both knit panel loops and the previous filament loop. Upon returning to the initial state, the crochet hook completes a full stitch. FIG. 14 depicts the process of knit shaping to fabricate panels with non-rectangular shapes. In order to fabricate non-rectangular panels and specifically curved or diagonal shapes, latch needles can be selectively engaged or disengaged to increase or decrease the width of knitted fabric, respectively. This process of adding or subtracting active latch needles into the knitting process is called shaping. The process of subtracting active latch needles results in fabric curling upon actuation. Alternatively, the process of adding active latch needles results in further contraction.

Figure 15B:
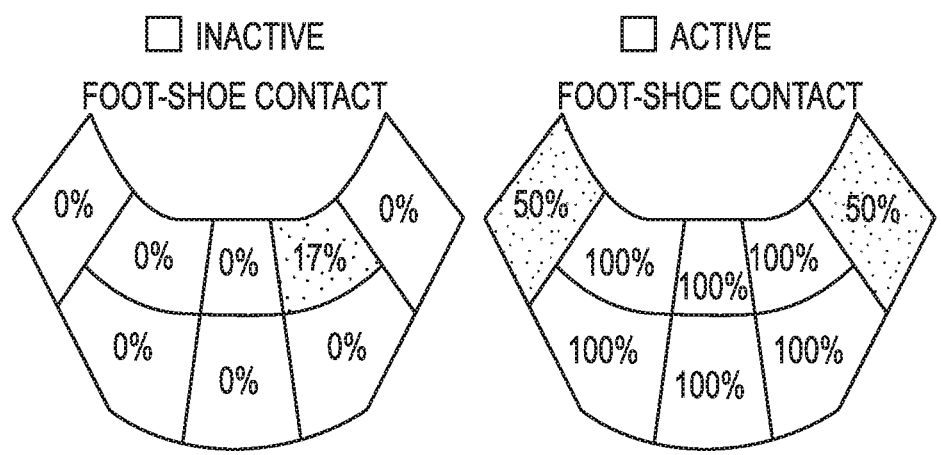
Figure 15C:
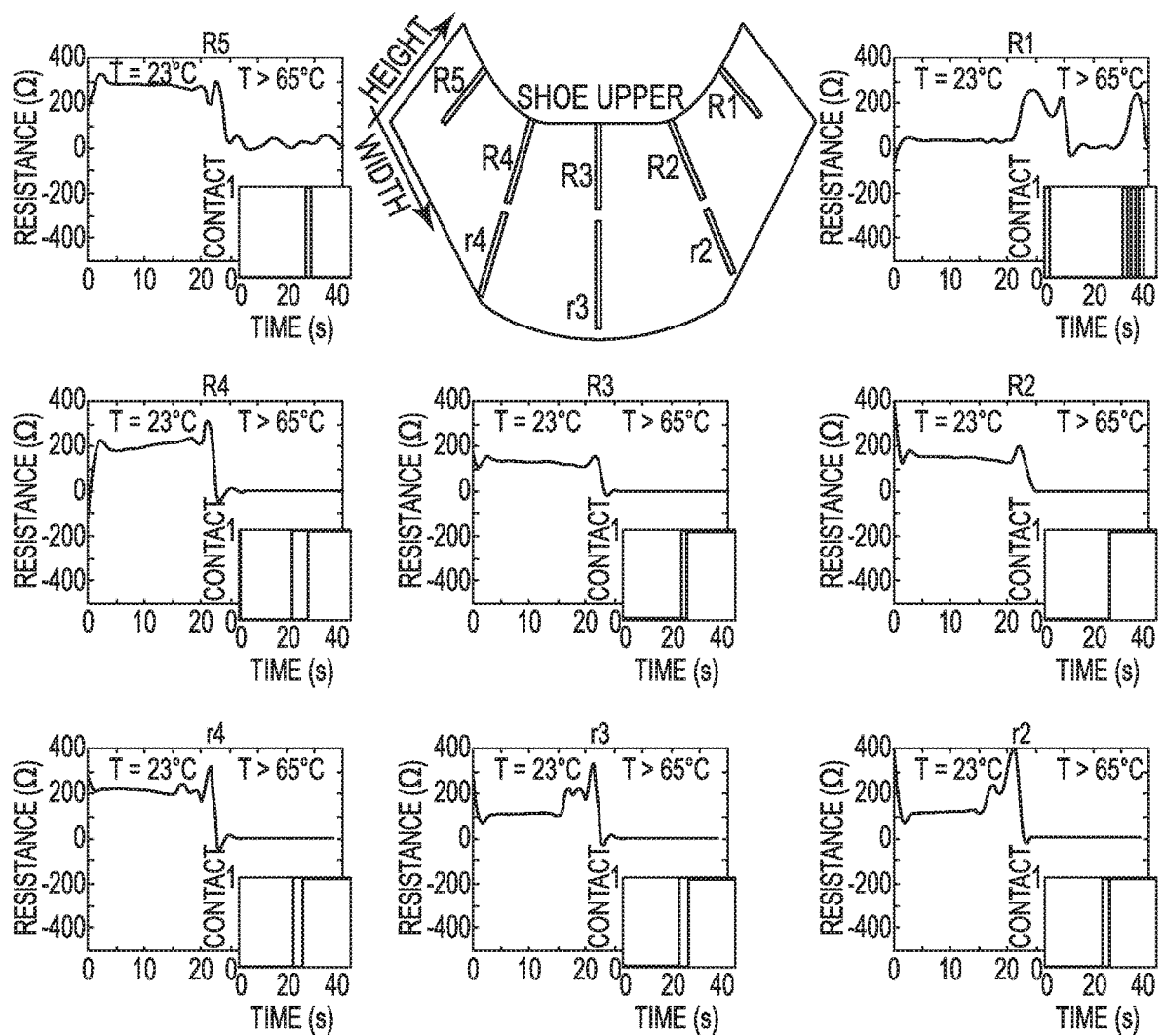

Taking all of these knitting patterns, materials, and iterative design processes in combination, complex topographies can be developed that correspond to anatomical structures that are not well-served by simple compression garments. FIGS. 15A and 15B show one example, a shoe 1500. Shoe 1500 includes first portion 1502, second portion 1504, and third portion 1506 that have different knit patterns and/or materials from one another. In fact, shoe 1500 can have dozens of different sections and knit patterns, in embodiments.

As shown in FIG. 15A, shoe 1500 is in a donning state (left), at which time the material that makes up the shoe 1500 is at low temperature and is loose. As such, donning the shoe 1500 is not difficult despite the fact that a foot is a relatively complex shape, and that feet include boney structures that cannot be compressed to fit into nonconforming garments. The middle image in FIG. 15A shows the shoe fully donned, and still at room temperature and therefore unactivated. The right-hand view of FIG. 15A shows the activated shoe 1500, which has tightened around the foot due to increased temperature.

FIG. 15B shows the level of contact between shoe 1500 and foot in the inactive (left) and activated (right) states. As shown in FIG. 15B, in the loose, relatively colder inactive state, there is between 0% and 20% contact between shoe 1500 and foot, whereas in the active state there is between 50% and 100% contact. Therefore shoe 1500 can provide a level of sensing, fit, comfort, or haptic feedback not possible in an untightened shoe. Shoes made solely of passive materials typically lack this level of contact at all areas of the shoe because of differences between each person's foot and the assumed shape inherent in the shoe's design. Even the use of passive compressive material lacks such good contact at all positions because of bridging effects across concave portions of the foot.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

We claim:

1. A method for forming a topographically conforming garment, the method comprising:
   collecting anthropometric data from a wearer to form a 3D topography, the anthropometric data comprising a series of closed loops arranged around a central axis;
   determining the second derivative of the radius of each one of the series of closed loops with respect to angle around the central axis to categorize sections of each of the series of closed loops into convex portions, concave portions, and flat portions;
   generating an initial design in which concave portions are knitted with Jersey purl stitch, flat sections are knitted with garter stitch, and convex portions are knitted with Jersey knit stitch, wherein the initial design includes a shape memory material incorporated into each of the sections such that exceeding a transition temperature of the shape memory material causes the Jersey purl stitch to contract and form a concave shape, the garter stitch to contract while remaining flat, and the Jersey knit stitch to contract and form a convex shape;
   calculating donning and doffing ease corresponding to the initial design; and
   iteratively modifying the design to achieve a desired minimum level of actuation contraction and a maximum size difference between the garment and the anthropometric data while maintaining a desired level of donning and doffing ease.

2. The method of claim 1, wherein iteratively modifying the design further comprises maintaining a filament diameter difference beneath a threshold.

3. The method of claim 1, wherein a plurality of panels are combined via stitching to form the iteratively modified design or the fabric, each of the panels comprising at least one of a convex portion, a concave portion, or a flat portion.

4. A method comprising:
   Providing a topographically conforming garment according to any of claim 1;
   arranging the topographically conforming garment on the wearer; and
   heating the garment to a transition temperature of the shape memory material of the concave portions, the convex portions, and the flat portions to achieve a desired compression profile on the wearer.

5. The method of claim 4, wherein the compression profile is uniform.

6. The method of claim 1, wherein the 3D topography corresponds to a foot.

7. The method of claim 1, wherein the 3D topography corresponds to a hand.

8. The method of claim 1, wherein the 3D topography corresponds to a leg.

9. The method of claim 1, wherein iteratively modifying the design is performed manually.

10. The method of claim 1, wherein iteratively modifying the design is performed by a machine learning algorithm.

11. A fabric configured to conform to a 3D topography, the fabric comprising:
    a first knitted portion having a first knit pattern corresponding to a concave portion of the 3D topography; and
    a second knitted portion having a second knit pattern corresponding to a convex portion of the 3D topography,
    wherein the first knitted portion and the second knitted portion each include a shape memory component, and wherein the knit pattern of the first knitted portion is different from the knit pattern of the second knitted portion such that upon actuation of the shape memory component the first portion contracts and forms a concave shape while the second portion contracts and forms a convex shape.

12. The fabric of claim 11, further comprising a third knitted portion having a third knit pattern corresponding to a flat portion of the 3D topography, wherein the third knit pattern includes a shape memory component and has a knit pattern that is different from the knit pattern of both the first knitted portion and the second knitted portion.

13. The fabric of claim 12, wherein the third knitted portion is configured to contract and remain substantially flat when the shape memory material exceeds a transition temperature.

14. The fabric of claim 13, wherein contraction of the shape memory causes the fabric to conform to the 3D topography with a uniform level of compression across both the concave portion and the convex portion.

15. The fabric of claim 11, further comprising a passive portion comprising a material that is not a shape memory material.

16. The fabric of claim 11, wherein the shape memory material includes multiple shape memory alloys, each of the multiple shape memory alloys having a corresponding transition temperature.

17. The fabric of claim 11, wherein the 3D topography corresponds to a foot.

18. The fabric of claim 11, wherein the 3D topography corresponds to a hand.

19. The fabric of claim 11, wherein the 3D topography corresponds to a leg.

* * * * *

UNITED STATES PATENT AND TRADEMARK OFFICE
CERTIFICATE OF CORRECTION

| | |
|---|---|
| PATENT NO. | : 11,993,874 B2 |
| APPLICATION NO. | : 17/753722 |
| DATED | : May 28, 2024 |
| INVENTOR(S) | : Kevin Eschen et al. |

Page 1 of 1

It is certified that error appears in the above-identified patent and that said Letters Patent is hereby corrected as shown below:

In the Specification

Add Government Support Clause (GSC) as follows at the beginning of the application:
*This invention was made with government support under*
*80NSSC17K0158 awarded by the National Aeronautics and Space Administration.*
*The government has certain rights in the invention.*

Signed and Sealed this
Twenty-third Day of July, 2024

Katherine Kelly Vidal
*Director of the United States Patent and Trademark Office*